US009464166B2

(12) United States Patent
Dakka et al.

(10) Patent No.: US 9,464,166 B2
(45) Date of Patent: *Oct. 11, 2016

(54) PRODUCTION AND USE OF 3,4' AND 4,4'-DIMETHYLBIPHENYL ISOMERS

(71) Applicant: ExxonMobil Chemical Patents Inc., Baytown, TX (US)

(72) Inventors: Jihad M. Dakka, Whitehouse Station, NJ (US); Lorenzo C. DeCaul, Langhorne, PA (US); Keith H. Kuechler, Friendswood, TX (US); Neeraj Sangar, League City, TX (US); Michael Salciccioli, Houston, TX (US); Alan A. Galuska, Huffman, TX (US); Gary D. Mohr, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/480,363

(22) Filed: Sep. 8, 2014

(65) Prior Publication Data

US 2015/0080545 A1 Mar. 19, 2015

Related U.S. Application Data

(63) Continuation-in-part of application No. 14/164,889, filed on Jan. 27, 2014, now Pat. No. 9,085,669, which is a continuation-in-part of application No. 13/751,835, filed on Jan. 28, 2013, now Pat. No. 8,829,093.

(60) Provisional application No. 62/026,889, filed on Jul. 21, 2014.

(51) Int. Cl.
| | |
|---|---|
| *C07C 2/74* | (2006.01) |
| *C08G 63/185* | (2006.01) |
| *C08G 63/199* | (2006.01) |
| *C08J 5/18* | (2006.01) |
| *D21H 27/20* | (2006.01) |
| *H01B 3/44* | (2006.01) |
| *C07C 51/265* | (2006.01) |
| *C07C 5/367* | (2006.01) |

(52) U.S. Cl.
CPC ............. *C08G 63/185* (2013.01); *C07C 2/74* (2013.01); *C07C 5/367* (2013.01); *C07C 51/265* (2013.01); *C08G 63/199* (2013.01); *C08J 5/18* (2013.01); *D21H 27/20* (2013.01); *H01B 3/443* (2013.01); *C07C 2101/14* (2013.01); *C08J 2327/06* (2013.01); *C08K 2201/014* (2013.01); *Y10T 428/2964* (2015.01)

(58) Field of Classification Search
USPC ........................................................ 585/320
See application file for complete search history.

(56) References Cited

U.S. PATENT DOCUMENTS

| | | | |
|---|---|---|---|
| 2,520,084 A | 8/1950 | Dazzi | |
| 2,976,266 A | 3/1961 | Lytton et al. | |
| 3,296,065 A | 1/1967 | O'Brien et al. | |
| 3,842,040 A | 10/1974 | Browne | |
| 3,842,041 A | 10/1974 | Browne | |
| 3,950,434 A | 4/1976 | Kominami et al. | |
| 3,962,362 A * | 6/1976 | Suggitt ............ | C07C 2/74 585/252 |
| 4,959,450 A | 9/1990 | Morris et al. | |
| 5,138,022 A | 8/1992 | Mang et al. | |
| 6,037,513 A | 3/2000 | Chang et al. | |
| 6,433,236 B1 * | 8/2002 | Schiraldi ........... | C07C 5/2756 568/722 |
| 7,579,511 B1 | 8/2009 | Dakka et al. | |
| 2014/0058143 A1 | 2/2014 | Yamamoto et al. | |
| 2014/0212666 A1 | 7/2014 | Dakka et al. | |
| 2014/0275609 A1 | 9/2014 | Dakka et al. | |

FOREIGN PATENT DOCUMENTS

| | | |
|---|---|---|
| JP | 2003 246755 | 9/2003 |
| WO | WO 97/49654 | 12/1997 |
| WO | WO 2014/117076 | 7/2014 |
| WO | WO 2014/159094 | 10/2014 |
| WO | WO 2014/159106 | 10/2014 |

OTHER PUBLICATIONS

Brechtelsbauer et al., "Shape selective methylation of biphenyl within zeolites: An example of transition state selectivity," Applied Catalysis A: General, vol. 161, 1997, pp. 79-92.
Kamiyama et al, "Hydroalkylation of Benzenes with Pd-Al$_2$O$_3$ and NaCl-AlCl$_3$," Chemistry Letters, 1979, pp. 261-264.
Ryabov et al., "Palladium(II)-Catalyzed Oxidation of Substituted Benzenes to Biaryls by Tris(trifluroacetato)Thallium(III)," Tetrahedron Letters, vol. 22, No. 38, 1981, pp. 3793-3796.
Shen et al., "Shape-selective synthesis of 4,4-dimethylbiphenyl, 1, Methylation of 4-methylbiphenyl over modified zeiolite catalysts," Catalysis Letters, vol. 65, 2000, pp. 147-151.

(Continued)

*Primary Examiner* — Scarlett Goon
*Assistant Examiner* — Ana Z Muresan

(57) ABSTRACT

In a process for producing 3,4' and/or 4,4' dimethyl-substituted biphenyl compounds, a feed comprising toluene is contacted with hydrogen in the presence of a hydroalkylation catalyst under conditions effective to produce a hydroalkylation reaction product comprising (methylcyclohexyl)toluenes. At least part of the hydroalkylation reaction product is dehydrogenated in the presence of a dehydrogenation catalyst under conditions effective to produce a dehydrogenation reaction product comprising a mixture of dimethyl-substituted biphenyl isomers. The dehydrogenation reaction product is then separated into at least a first stream containing at least 50% of 3,4' and 4,4' dimethylbiphenyl isomers by weight of the first stream and at least one second stream comprising one or more 2,x' (where x' is 2', 3', or 4') and 3,3' dimethylbiphenyl isomers.

17 Claims, 7 Drawing Sheets

(56) References Cited

OTHER PUBLICATIONS

U.S. Appl. No. 13/751,835, filed Jan. 28, 2013, Dakka et al.
U.S. Appl. No. 14/164,889, filed Jan. 27, 2014, Dakka et al.
U.S. Appl. No. 14/201,224, filed Mar. 7, 2014, Dakka et al.
U.S. Appl. No. 14/201,287, filed Mar. 7, 2014, Dakka et al.
U.S. Appl. No. 14/480,379, filed Sep. 8, 2014, Dakka et al.
U.S. Appl. No. 62/026,889, filed Jul. 21, 2014, Dakka et al.

Izard, E. F., "*Effect of Chemical Structure on Physical Properties of Isomeric Polyesters*," Journal of Polymer Science Part A: Polymer Science, vol. 9, Issue 1 (1952), pp. 35-39.
Krigbaum et al., Journal of Polymer Science: Polymer Letters Edition, vol. 20, Issue 2 (1982), pp. 109-115.
Meurisse et al., "*Polymers with Mesogenic Elements and Flexible Spacers in the Main Chain: Aromatic-Aliphatic Polyesters*," The British Polymer Journal, vol. 13, Issue 2 (1981), pp. 55-63.

* cited by examiner

PRODUCTION AND USE OF 3,4' AND 4,4'-DIMETHYLBIPHENYL ISOMERS

PRIORITY

This application is a continuation in part of U.S. Ser. No. 14/164,889, filed Jan. 27, 2014, which is a continuation-in-part of U.S. application Ser. No. 13/751,835, filed Jan. 28, 2013 and this application claims the benefit of and priority to U.S. Provisional Application No. 62/026,889, filed Jul. 21, 2014, the disclosures of which are fully incorporated herein by reference. This invention is also related to concurrently filed U.S. Ser. No. 14/480,379, filed Sep. 8, 2014.

FIELD

This disclosure relates to the production of 3,4'and 4,4'-dimethylbiphenyl isomer mixtures and their use in the production of plasticizers and polyesters.

BACKGROUND

Dimethylbiphenyl (DMBP) compounds are useful intermediates in the production of a variety of commercially valuable products, including polyesters and plasticizers for PVC and other polymer compositions. For example, DMBP can readily be converted to an ester plasticizer by a process comprising oxidation of the DMBP to produce the corresponding mono- or dicarboxylic acid followed by esterification with a long chain alcohol. For certain uses, it is important to maximize the level of the 3,4'-isomer and particularly the 4,4'-isomer in the product.

In addition, 4,4'-diphenyl-dicarboxylic acid, optionally together with diphenyl-3,4'-dicarboxylic acid, is a potential precursor, either alone or as a modifier for polyethylene terephthalate (PET), in the production of polyester fibers, engineering plastics, liquid crystal polymers for electronic and mechanical devices, and films with high heat resistance and strength.

For example, homopolyesters of 4,4'-biphenyl dicarboxylic acid (BDA) and various aliphatic diols have been disclosed in the literature. For example, Ezard disclosed homopolyester between 4,4'-biphenyl dicarboxylic acid and ethylene glycol in the *Journal of Polymer Science*, 9, 35 (1952). In the *British Polymer Journal*, 13, 57 (1981), Meurisse et al. disclosed homopolyesters made from 4,4'-biphenyl dicarboxylic acid and a number of diols including ethylene glycol, 1,4-butanediol and 1,6-hexanediol. Homopolyesters of 4,4'-biphenyl dicarboxylic acid and ethylene glycol were also disclosed in U.S. Pat. Nos. 3,842,040 and 3,842,041.

Copolyesters of 4,4'-biphenyl dicarboxylic acid and mixtures of aliphatic diols are also disclosed in the literature, for example, in U.S. Pat. No. 2,976,266. Morris et al. disclosed copolyesters from 4,4'-biphenyl dicarboxylic acid, and the mixtures of 1,4-cyclohexanedimethanol and 1,6-hexanediol in U.S. Pat. No. 4,959,450. Copolyesters of 4,4'-biphenyl dicarboxylic acid and terephthalic acid, and certain aliphatic diols are disclosed in the literature, for example, in the *Journal of Polymer Science, Polym. Letters*, 20, 109 (1982) by Krigbaum et al. U.S. Pat. No. 5,138,022 disclosed copolyester of 3,4' biphenyl dicarboxylic acid and optionally 4,4'-biphenyl dicarboxylic acid, and certain aliphatic diols like ethylene glycol, 1,4-butanediol, and 1,4-cyclohexanedimethanol.

As disclosed in our co-pending U.S. patent application Ser. Nos. 14/201,287 and 14/201,224, both filed Mar. 7, 2014, dimethyl biphenyl may be produced by hydroalkylation of toluene followed by dehydrogenation of the resulting (methylcyclohexyl)toluene (MCHT). However, even using a selective molecular sieve catalyst for the hydroalkylation step, this process tends to yield a mixture of all six DMBP isomers, namely 2,2', 2,3', 2,4', 3,3', 3,4' and 4,4' DMBP, in which the 2,X' (where X' is 2', 3' or 4') and 3,3' DMBP isomer content may be 50% by weight or more of the total DMBP product. The entire disclosures of application Ser. Nos. 14/201,287 and 14/201,224 are incorporated herein by reference in their entirety.

Alternative routes via benzene are described in co-pending U.S. patent application Ser. No. 14/164,889, filed Jan. 27, 2014, in which the benzene is initially converted to biphenyl, either by oxidative coupling or by hydroalkylation to cyclohexyl benzene (CHB) followed by dehydrogenation of the CHB, and then the biphenyl is alkylated with methanol. Again, however, the alkylated product is a mixture of DMBP isomers, in which the levels of the desired 3,4' and 4,4' isomers may be lower than 50% by weight of the total DMBP product.

There is, therefore, interest in developing a process for producing dimethyl-substituted biphenyl compounds in which the yield of 3,4' isomer, and particularly the 4,4' isomer, is maximized.

SUMMARY

In one aspect, the invention resides a process for producing 3,4' and/or 4,4' dimethyl-substituted biphenyl compounds, the process comprising:

(a1) contacting a feed comprising toluene with hydrogen in the presence of a hydroalkylation catalyst under conditions effective to produce a hydroalkylation reaction product comprising (methylcyclohexyl)toluenes;

(b1) dehydrogenating at least part of the hydroalkylation reaction product in the presence of a dehydrogenation catalyst under conditions effective to produce a dehydrogenation reaction product comprising a mixture of dimethyl-substituted biphenyl isomers; and (c1) separating the dehydrogenation reaction product into at least a first stream containing at least 50% of 3,4' and 4,4' dimethylbiphenyl isomers by weight of the first stream and at least one second stream comprising one or more 2,X' (where X' is 2', 3', or 4') and 3,3' dimethylbiphenyl isomers.

In a further aspect, the invention resides a process for producing 3,4' and/or 4,4' dimethyl-substituted biphenyl compounds, the process comprising:

(a2) contacting a feed comprising benzene with hydrogen in the presence of a hydroalkylation catalyst under conditions effective to produce a hydroalkylation reaction product comprising cyclohexylbenzenes;

(b2) dehydrogenating at least part of the hydroalkylation reaction product in the presence of a dehydrogenation catalyst under conditions effective to produce a dehydrogenation reaction product comprising biphenyl;

(c2) reacting at least part of the dehydrogenation reaction product with a methylating agent in the presence of an alkylation catalyst under conditions effective to produce a methylation reaction product comprising a mixture of dimethyl-substituted biphenyl isomers; and (d2) separating the methylation reaction product into at least a first stream containing at least 50% of 3,4' and 4,4' dimethylbiphenyl isomers by weight of the first stream and at least one second stream comprising one or more 2,X' (where X' is 2', 3', or 4') and 3,3' dimethylbiphenyl isomers.

In yet a further aspect, the invention resides a process for producing 3,4' and/or 4,4' dimethyl-substituted biphenyl compounds, the process comprising:

(a3) oxidizing a feed comprising benzene in the presence of a oxidative coupling catalyst under conditions effective to produce a oxidation reaction product comprising biphenyl;

(b3) reacting at least part of the oxidation reaction product with a methylating agent in the presence of an alkylation catalyst under conditions effective to produce a methylation reaction product comprising a mixture of dimethyl-substituted biphenyl isomers; and (c3) separating the methylation reaction product into at least a first stream comprising at least 50% of 3,4' and 4,4' dimethylbiphenyl isomers by weight of the first stream and at least one second stream comprising one or more 2,X' (where X' is 2', 3', or 4') and 3,3' dimethylbiphenyl isomers.

In another aspect, the invention resides in a mixture comprising at least 50 wt %, preferably from 90 to 99 wt %, of a compound of the formula:

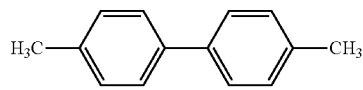

and at least 1 wt %, preferably from 1 to 10 wt %, of a compound of the formula:

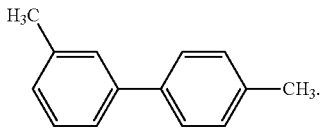

In a further aspect, the invention resides in a mixture comprising at least 50 wt %, preferably from 90 to 99 wt %, of a compound of the formula:

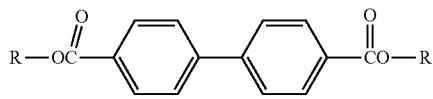

and at least 1 wt %, preferably from 1 to 10 wt %, of a compound of the formula:

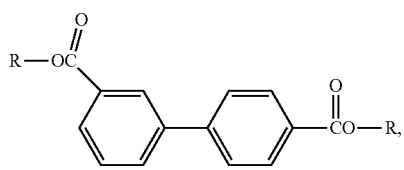

wherein each R is, independently, a $C_1$ to $C_{16}$ hydrocarbyl.

In yet a further aspect, the invention resides in a mixture comprising at least 50 wt %, preferably from 90 to 99 wt %, of one or more compounds having the formulas:

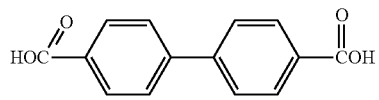

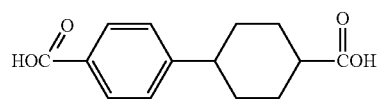

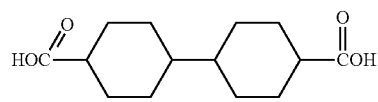

and at least 1 wt %, preferably from 1 to 10 wt %, of one or more compounds having the formulas:

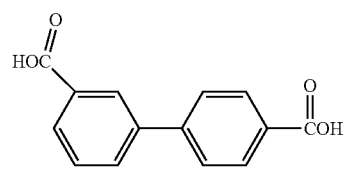

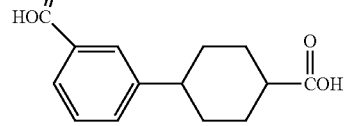

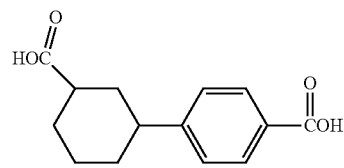

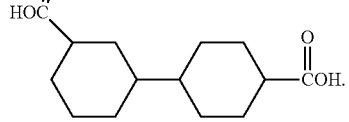

In one embodiment, the invention resides in a mixture comprising at least 50 wt %, preferably from 90 to 99 wt %, of a compound having the formula:

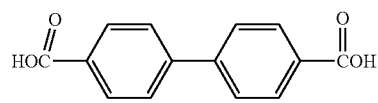

and at least 1 wt %, preferably from 1 to 10 wt %, of a compound having the formula:

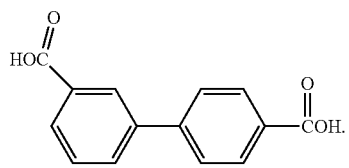

In another embodiment, the invention resides in a mixture comprising at least 50 wt %, preferably from 90 to 99 wt %, of a compound having the formula:

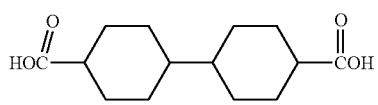

and at least 1 wt %, preferably from 1 to 10 wt %, of a compound having the formula:

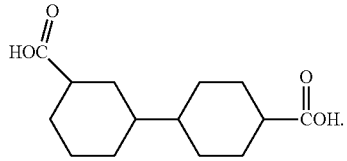

In yet another aspect, the invention resides in a mixture comprising at least 50 wt %, preferably from 90 to 99 wt %, of one or more compounds having the formulas:

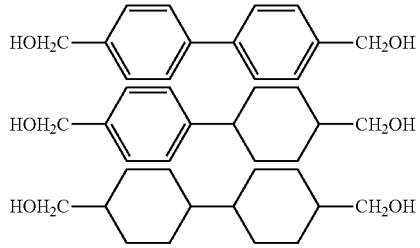

and at least 1 wt %, preferably from 1 to 10 wt %, of one or more compounds having the formulas:

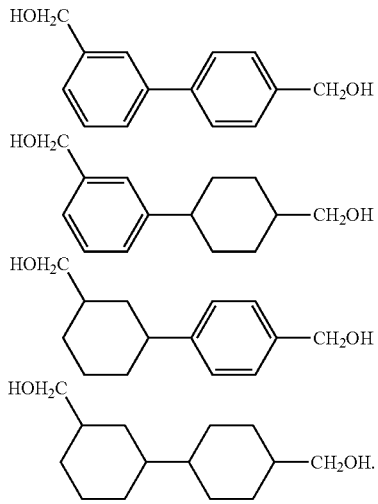

In one embodiment, the invention resides in a mixture comprising at least 50 wt %, preferably from 90 to 99 wt %, of a compound having the formula:

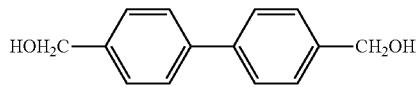

and at least 1 wt %, preferably from 1 to 10 wt %, of a compound having the formula:

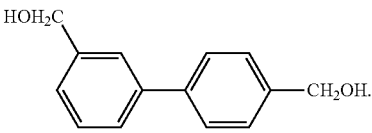 [SMILES: OCc1ccc(-c2cccc(CO)c2)cc1]

In a further embodiment, the invention resides in a mixture comprising at least 50 wt %, preferably from 90 to 99 wt %, of a compound having the formula:

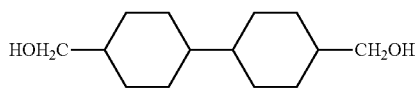

and at least 1 wt %, preferably from 1 to 10 wt %, of a compound having the formula:

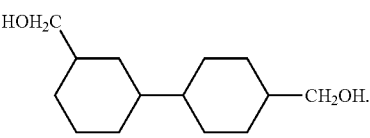 [SMILES: OCC1CCC(C2CCCC(CO)C2)CC1]

In other embodiments, the invention resides in polyesters produced from the diacids and/or the dialcohols described herein.

DETAILED DESCRIPTION OF THE EMBODIMENTS

Figure 1:
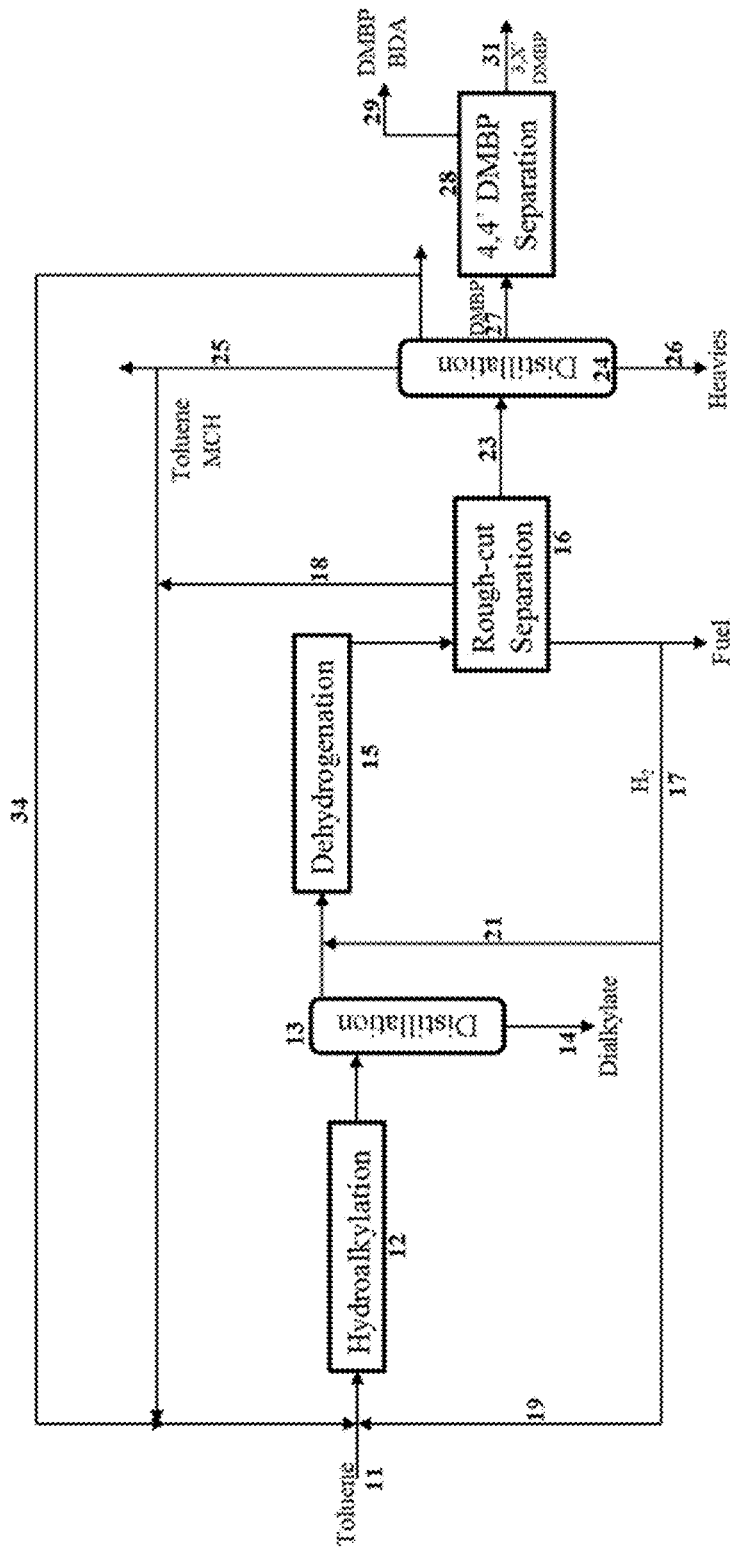
FIG. 1 is a flow diagram of a process of producing 4,4'-dimethylbiphenyl from toluene according to one embodiment of the invention.
Figure 2:
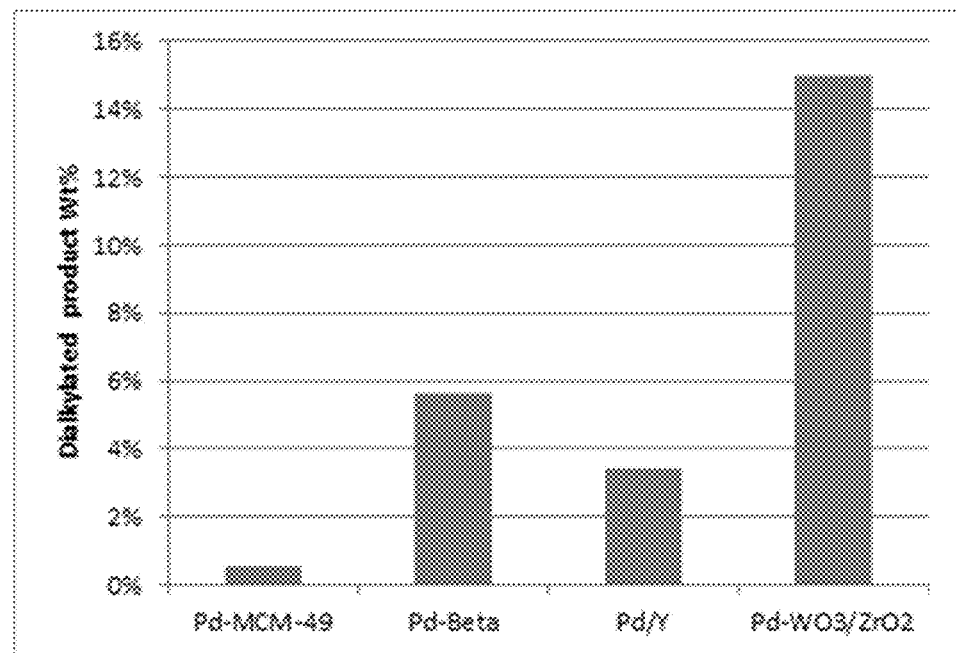
FIG. 2 is a bar graph comparing the amount of di(methylcyclohexyl)toluenes produced in the hydroalkylation of toluene over the catalysts of Examples 1 to 4.
Figure 3:
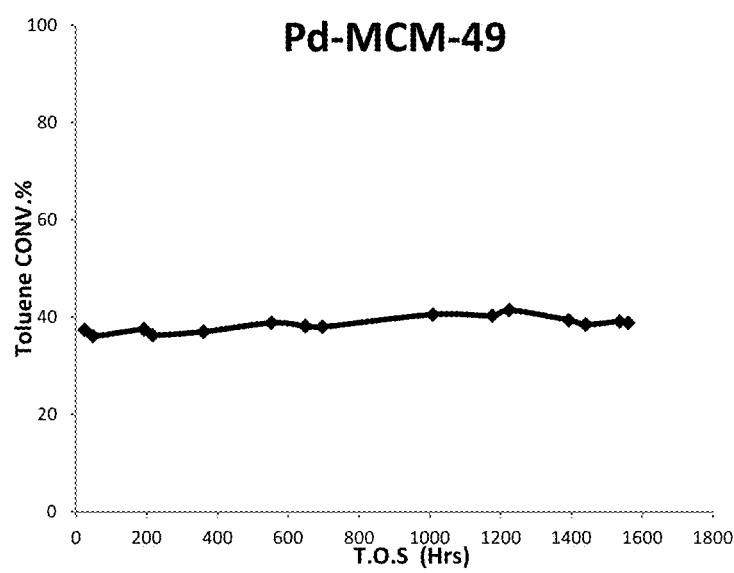
FIG. 3 is a graph of toluene conversion against time on stream (TOS) in the hydroalkylation of toluene over the Pd-MCM-49 catalyst of Example 1.
Figure 4:
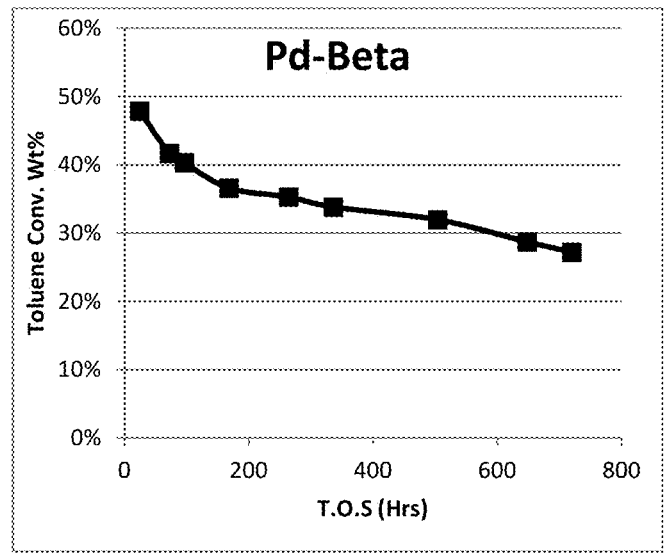
FIG. 4 is a graph of toluene conversion against time on stream (TOS) in the hydroalkylation of toluene over the Pd-beta catalyst of Example 2.
Figure 5:
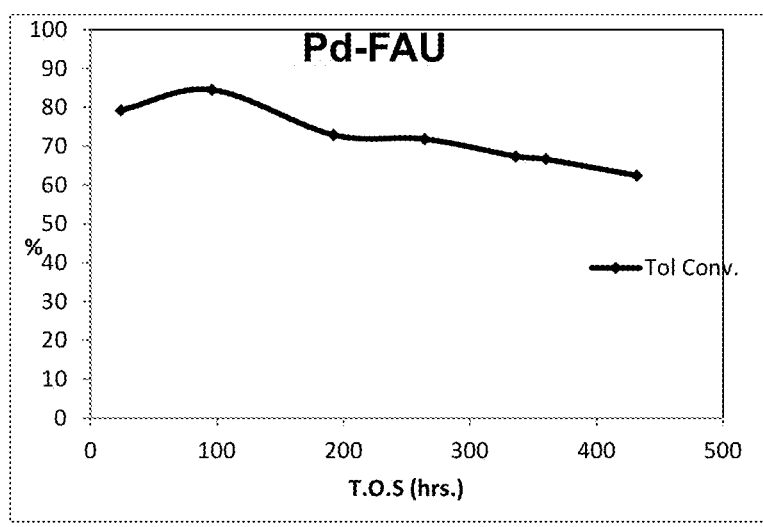
FIG. 5 is a graph of toluene conversion against time on stream (TOS) in the hydroalkylation of toluene over the Pd-Y catalyst of Example 3.
Figure 6:
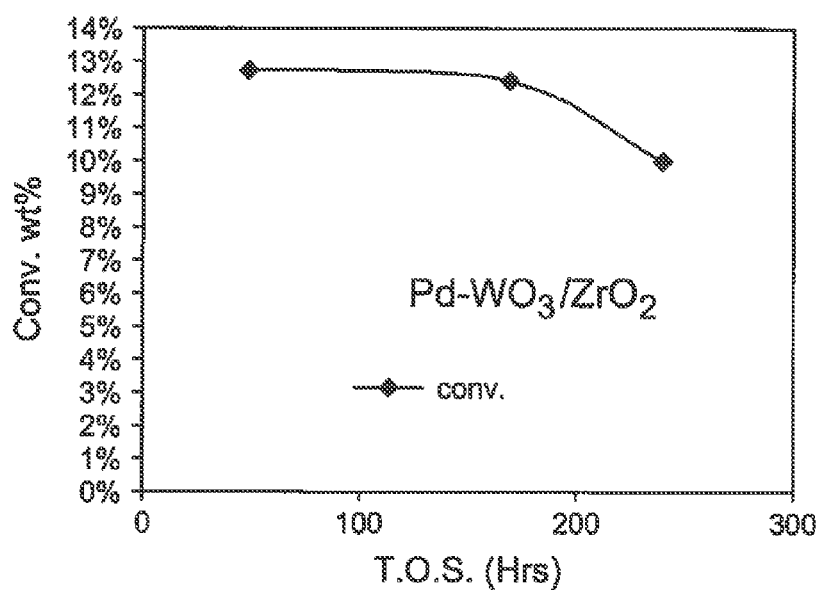
FIG. 6 is a graph of toluene conversion against time on stream (TOS) in the hydroalkylation of toluene over the Pd-WO$_3$/ZrO$_2$ catalyst of Example 4.

Described herein are (a) processes of producing 3,4' and/or 4,4' dimethyl-substituted biphenyl compounds from low cost feeds, particularly toluene and/or benzene, (b) novel isomer mixtures produced by these processes and (c) use of the resultant isomer mixtures in producing biphenyl dicarboxylic acids and derivatives thereof useful in the manufacture of plasticizers and polyesters.

Production of Dimethyl-Substituted Biphenyl Compounds from Toluene

In one embodiment, the feed employed in the present process comprises toluene, which is initially converted to (methylcyclohexyl)toluenes by reaction with hydrogen over a hydroalkylation catalyst according to the following reaction:

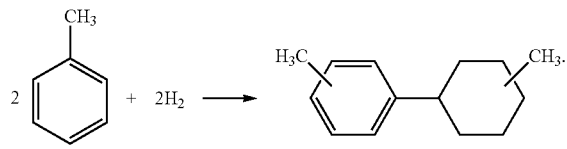

The catalyst employed in the hydroalkylation reaction is a bifunctional catalyst comprising a hydrogenation component and a solid acid alkylation component, typically a molecular sieve. The catalyst may also include a binder such as clay, alumina, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Any known hydrogenation metal or compound thereof can be employed as the hydrogenation component of the catalyst, although suitable metals include palladium, ruthenium, nickel, zinc, tin, and cobalt, with palladium being particularly advantageous. In certain embodiments, the amount of hydrogenation metal present in the catalyst is between about 0.05 and about 10 wt %, such as between about 0.1 and about 5 wt %, of the catalyst.

In one embodiment, the solid acid alkylation component comprises a large pore molecular sieve having a Constraint Index (as defined in U.S. Pat. No. 4,016,218) less than 2. Suitable large pore molecular sieves include zeolite beta, zeolite Y, Ultrastable Y (USY), Dealuminized Y (Deal Y), mordenite, ZSM-3, ZSM-4, ZSM-18, and ZSM-20. Zeolite ZSM-4 is described in U.S. Pat. No. 4,021,447. Zeolite ZSM-20 is described in U.S. Pat. No. 3,972,983. Zeolite Beta is described in U.S. Pat. No. 3,308,069, and Re. No. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Zeolite UHP-Y is described in U.S. Pat. No. 4,401,556. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104.

In another, more preferred embodiment, the solid acid alkylation component comprises a molecular sieve of the MCM-22 family. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697) and mixtures thereof.

In addition to the toluene and hydrogen, the feed to the hydroalkylation reaction may include benzene and/or xylene which can undergo hydroalkylation to produce various methylated cyclohexylbenzene molecules of $C_{12}$ to $C_{16}$ carbon number. A diluent, which is substantially inert under hydroalkylation conditions, may also be included in the hydroalkylation feed. In certain embodiments, the diluent is a hydrocarbon, in which the desired cycloalkylaromatic product is soluble, such as a straight chain paraffinic hydrocarbon, a branched chain paraffinic hydrocarbon, and/or a cyclic paraffinic hydrocarbon. Examples of suitable diluents are decane and cyclohexane. Although the amount of diluent is not narrowly defined, desirably the diluent is added in an amount such that the weight ratio of the diluent to the aromatic compound is at least 1:100; for example at least 1:10, but no more than 10:1, desirably no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 and about 7,000 kPa, such as between about 500 and about 5,000 kPa. The molar ratio of hydrogen to aromatic feed is typically from about 0.15:1 to about 15:1.

In the present process, it is found that MCM-22 family molecular sieves are particularly active and stable catalysts for the hydroalkylation of toluene or xylene. In addition, catalysts containing MCM-22 family molecular sieves exhibit improved selectivity to the 3,3'-dimethyl, the 3,4'-dimethyl, the 4,3'-dimethyl and the 4,4'-dimethyl isomers in the hydroalkylation product, while at the same time reducing the formation of fully saturated and heavy by-products. For example, using an MCM-22 family molecular sieve with a toluene feed, it is found that the hydroalkylation reaction product may comprise:

at least 60 wt %, such as at least 70 wt %, for example at least 80 wt % of the 3,3', 3,4', 4,3' and 4,4'-isomers of (methylcyclohexyl)toluene based on the total weight of all the (methylcyclohexyl)toluene isomers;

less than 40 wt %, such as less than 30 wt %, for example from 15 to 25 wt % of the 2,2', 2,3', and 2,4'-isomers of (methylcyclohexyl)toluene based on the total weight of all the (methylcyclohexyl)toluene isomers;

less than 30 wt % of methylcyclohexane and less than 2% of dimethylbicyclohexane compounds; and less than 1 wt % of compounds containing in excess of 14 carbon atoms, such as di(methylcyclohexyl)toluene.

The hydroalkylation reaction product may also contain significant amounts of residual toluene, for example up to 50 wt %, such as up to 90 wt %, typically from 60 to 80 wt % of residual toluene based on the total weight of the hydroalkylation reaction product. The residual toluene can readily be removed from the reaction effluent by, for example, distillation. The residual toluene can then be recycled to the hydroalkylation reactor, together with some or all of any unreacted hydrogen. In some embodiments, it may be desirable to remove the $C_{14}+$ reaction products, such as di(methylcyclohexyl)toluene, for example, by distillation.

The remainder of the hydroalkylation reaction effluent, composed mainly of (methylcyclohexyl)toluenes, is then dehydrogenated to convert the (methylcyclohexyl)toluenes to the corresponding methyl-substituted biphenyl compounds. The dehydrogenation is conveniently conducted at a temperature from about 200° C. to about 600° C. and a pressure from about 100 kPa to about 3550 kPa (atmospheric to about 500 psig) in the presence of dehydrogenation catalyst. A suitable dehydrogenation catalyst comprises one or more elements or compounds thereof selected from Group 10 of the Periodic Table of Elements, for example platinum, on a support, such as silica, alumina or carbon nanotubes. In one embodiment, the Group 10 element is present in an amount from 0.1 to 5 wt % of the catalyst. In some cases, the dehydrogenation catalyst may also include tin or a tin compound to improve the selectivity to the desired methyl-substituted biphenyl product. In one embodiment, the tin is present in an amount from 0.05 to 2.5 wt % of the catalyst.

Particularly using an MCM-22 family-based catalyst for the upstream hydroalkylation reaction, the product of the dehydrogenation step comprises dimethylbiphenyl compounds in which the concentration of the 3,3'-, 3,4'- and 4,4' isomers is at least 50 wt %, such as at least 60 wt %, for example at least 70 wt % based on the total weight of dimethylbiphenyl compounds. Typically, the concentration of the 2,X'-dimethylbiphenyl isomers in the dehydrogenation product is less than 50 wt %, such as less than 30 wt %, for example from 5 to 25 wt % based on the total weight of dimethylbiphenyl compounds.

Production of Dimethyl-Substituted Biphenyl Compounds from Benzene

In other embodiments, the present process for producing dimethyl-substituted biphenyl compounds employs benzene as the feed and comprises initially converting the benzene to biphenyl. For example, benzene can be converted directly to biphenyl by reaction with oxygen over an oxidative coupling catalyst as follows:

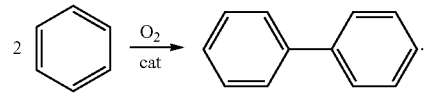

Details of the oxidative coupling of benzene can be found in Ukhopadhyay, Sudip; Rothenberg, Gadi; Gitis, Diana; Sasson, Yoel, Casali Institute of Applied Chemistry, Hebrew University of Jerusalem, Israel, Journal of Organic Chemistry (2000), 65(10), pp. 3107-3110, incorporated herein by reference.

Alternatively, benzene can be converted to biphenyl by hydroalkylation to cyclohexylbenzene according to the reaction:

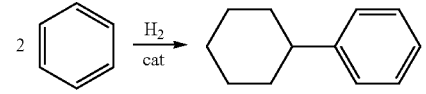

followed by dehydrogenation of the cyclohexylbenzene as follows;

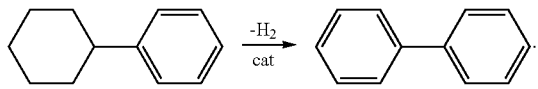

In such a process, the benzene hydroalkylation can be conducted in the same manner as described above for the hydroalkylation of toluene, while the dehydrogenation of the cyclohexylbenzene can be conducted in the same manner as described above for the dehydrogenation of (methylcyclohexyl)toluene.

In either case, the biphenyl product of the oxidative coupling step or the hydroalkylation/dehydrogenation sequence is then methylated, for example with methanol, to produce dimethylbiphenyl. Any known alkylation catalyst can be used for the methylation reaction, such as an intermediate pore molecular sieve having a Constraint Index (as defined in U.S. Pat. No. 4,016,218) of 3 to 12, for example ZSM-5.

The composition of the methylated product will depend on the catalyst and conditions employed in the methylation reaction, but inevitably will comprise a mixture of the different isomers of dimethylbiphenyl. Typically, the methylated product will contain from 50 to 100 wt % of 3,3'-, 3,4'- and 4,4' dimethylbiphenyl isomers and from 0 to 50 wt % of 2,X' (where X' is 2', 3' or 4')-dimethylbiphenyl isomers based on the total weight of dimethylbiphenyl compounds in the methylation product.

Separation of 3,4' and 4,4'-Dimethylbiphenyl Isomers

Depending on the intended use of the dimethylbiphenyl product, it is important to provide a simple and effective method of separating and recovering the 3,4' and 4,4' dimethylbiphenyl isomers and, in some embodiments, of separately isolating a 3,4' dimethylbiphenyl isomer stream and a 4,4' dimethylbiphenyl isomer stream. In addition, as will be discussed below, it may be desirable to convert some or all the remaining 2,X' (where X' is 2', 3' or 4') dimethylbiphenyl isomers into the more desirable 3,Y' (where Y' is 3' or 4') and 4,4' dimethylbiphenyl isomers.

Irrespective of the process used, the raw dimethylbiphenyl product from the production sequences described will contain unreacted components and by-products in addition to a mixture of dimethylbiphenyl isomers. For example, where the initial feed comprises toluene and the production sequence involves hydroalkylation to MCHT and dehydrogenation of the MCHT, the raw dimethylbiphenyl product will tend to contain residual toluene and MCHT and by-products including hydrogen, methylcyclohexane dimethylcyclohexylbenzene, and $C_{15}+$ heavy hydrocarbons in addition to the target dimethylbiphenyl isomers. Thus, in some embodiments, prior to any separation of the dimethylbiphenyl isomers, the raw product of the MCHT dehydrogenation is subjected to a rough cut separation to remove at least part of the residues and by-products with significantly different boiling points from the dimethylbiphenyl isomers. For example, the hydrogen by-product can be removed and recycled to the hydroalkylation and/or MCHT dehydrogenation steps, while residual toluene and methylcyclohexane by-product can be removed and recycled to the hydroalkylation step. Similarly, part of the heavy ($C_{15}+$) components can be removed in the rough cut separation and can be recovered for use as a fuel or can be reacted with toluene over a transalkylation catalyst to convert some of the dialkylate to additional MCHT. A suitable rough cut separation can be achieved by distillation. For example, the $H_2$ and $C_7$ components can be stripped from the $C_{12+}$ components without reflux.

After partial removal of the by-products and residual components in the rough cut separation, the remaining dimethylbiphenyl product is subjected to a first DMBP separation step, in which the product is separated into at least a first stream rich in 3,4' and 4,4' dimethylbiphenyl and at least one second stream comprising one or more 2,x' (where x' is 2', 3', or 4') and 3,3' dimethylbiphenyl isomers. The second stream will also typically contain most of the unreacted MCHT and most of the dimethylcyclohexylbenzene by-product in the raw dimethylbiphenyl product. A suitable process for effecting this initial separation is crystallization and/or distillation operating below or, more preferably at, atmospheric pressure. Thus, the normal boiling points and temperatures of fusion of the 2,x', 3,3', 3,4'- and 4,4'-dimethylbiphenyl isomers are shown in Table 1 below:

TABLE 1

| Isomer | Normal Boiling Point (K) | Fusion Temperature (K) |
|---|---|---|
| 2,2' | 531 | 320 |
| 2,3' | 546 | |
| 2,4' | 554 | |
| 3,3' | 559 | 278 |
| 3,4' | 569 | 283 |
| 4,4' | 568 | 394 |

In embodiments, the first stream contains at least 50%, such as at least 60%, for example at least 70%, such as at least 80%, for example at least 90%, of 3,4' and 4,4' dimethylbiphenyl isomers by weight of the first stream. In terms of ranges, the first stream may contain from 50 to 95%, such as from 70 to 95%, for example from 80 to 95%, of 3,4' and 4,4' dimethylbiphenyl by weight of the first stream. In terms of the amounts of the specific isomers, the first stream may contain at least 50 wt %, preferably at least 90 wt %, preferably from 90 to 100 wt %, of a compound of the formula:

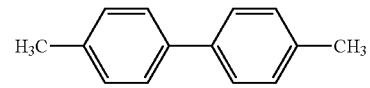

and and at least 1 wt %, such as at least 10 wt %, preferably from 10 to 50 wt %, of a compound of the formula:

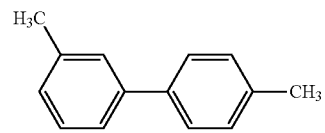

based on the total weight of the first stream. In addition, the first stream may also contain up to 40%, such as from 0 to 40%, for example from 1 to 10%, of 3,3' dimethylbiphenyl by weight of the first stream.

In embodiments, the second stream contains at least 30%, such as from 30 to 50%, of the 2,X' dimethylbiphenyl isomers and at least 30%, such as from 30 to 50%, 3,3' dimethylbiphenyl, with all percentages being by weight based on the total weight of the second stream. Where the DMBP synthesis route includes toluene hydroalkylation followed by dehydrogenation of MCHT, the second stream will also typically contain most of the unreacted MCHT and most of the dimethylcyclohexylbenzene by-product in the raw dimethylbiphenyl product. Part or all of the 2,X' dimethylbiphenyl isomers in the second stream may be converted, as described below, to 3,Y' (where Y' is 3' or 4') and 4,4' dimethylbiphenyl isomers. The converted stream can then be recycled back to the rough cut separation or to the first DMBP separation step to recover the additional 3,Y' and 4,4' isomers.

A light overhead stream may also be removed in the initial separation step to recover any residual toluene remaining from the rough cut separation. This light overhead stream may be recycled to the hydroalkylation step.

The initial separation may also be used to remove additional heavy components remaining in the raw dimethylbiphenyl product after the rough cut separation. These heavy components may be directed to fuel use.

In certain embodiments, part or all of the first stream can be recovered and, optionally after further purification, can be forwarded for certain end-use applications, such as the production of plasticizers. In the latter case, the first stream can be subjected to oxidation to convert one or both the methyl groups to carboxylic acid group(s) and then the or each acid group can be esterified with a long chain alcohol, such as an OXO-alcohol. These processes are described in more detail below.

In other embodiments, part or all of the first stream is subjected to a second DMBP separation step to separate the first stream into a third stream rich in 4,4' dimethylbiphenyl and a fourth stream comprising 3,4' dimethylbiphenyl. Because of the differences in fusion temperatures noted in Table 1, the second DMBP separation is conveniently effected by fractional crystallization. In some embodiments, the fractional crystallization is assisted by the addition of a solvent, preferably a $C_3$ to $C_{12}$ aliphatic hydrocarbon, more preferably pentane and/or hexane, to the first stream. Suitable amounts for the solvent addition comprise as from 10 to 75%, for example from 25 to 50% solvent by weight of the first stream.

In embodiments, the 4,4' DMBP-rich third stream contains at least 70%, such as at least 80%, for example at least 90%, even up to 100%, of 4,4' dimethylbiphenyl by weight of the third stream. In terms of ranges, the third stream may contain from 70 to 100%, such as from 80 to 100%, for example from 95 to 100%, of 4,4' dimethylbiphenyl by weight of the first stream. In addition, the third stream will normally contain at least 1% and up to 30%, such as up to 20%, for example up to 10%, by weight of 3,4' dimethylbiphenyl by weight of the third stream. Typically, the third stream contains less than 5%, such as less than 1%, by weight, even no measurable amount of, 3,3' dimethylbiphenyl.

In embodiments, the fourth stream contains at least 70%, such as at least 80%, for example at least 90%, even up to 100%, of 3,4' dimethylbiphenyl by weight of the third stream. In terms of ranges, the fourth stream may contain from 70 to 100%, such as from 80 to 100%, for example from 90 to 100%, of 3,4' dimethylbiphenyl by weight of the fourth stream. In addition, the fourth stream may contain up to 30%, such as up to 20%, for example up to 10%, by weight of 3,3' dimethylbiphenyl by weight of the fourth stream. Typically, the fourth stream contains less than 10%, such as less than 5%, by weight, even no measurable amount of, 4,4' dimethylbiphenyl.

As will be discussed in more detail below, part or all of the third stream can be recovered and, optionally after further purification, can be forwarded for certain end-use applications, such as the production of polyesters. The third stream can also be used in the production of plasticizers in the same way as the first stream but, in general, this is not the highest value use of the third stream.

In certain embodiments, part or all of the fourth stream can be recovered and, optionally after further purification, can be forwarded for certain end-use applications, such as the production of plasticizers or, more preferably, polyesters. In other embodiments, the fourth stream is subjected to a third DMBP separation step to separate the fourth stream into a fifth stream rich in 3,4' dimethylbiphenyl and a sixth stream containing 3,3' dimethylbiphenyl. The third DMBP separation can be effected by distillation or fractional crystallization. In the latter case, the fractional crystallization may be assisted by the addition of a solvent, preferably a $C_3$ to $C_{12}$ aliphatic hydrocarbon, more preferably pentane and/or hexane, to the fourth stream. Suitable amounts for the solvent addition comprise as from 10 to 75%, for example from 25 to 50% solvent by weight of the fourth stream.

In embodiments, the 3,4' DMBP-rich fifth stream contains at least 80%, for example at least 90%, even up to 100%, of 3,4' dimethylbiphenyl by weight of the fifth stream. Typically, the fifth stream contains less than 20%, such as less than 10%, by weight, even no measurable amount of, 3,3' dimethylbiphenyl. The fifth stream may be recovered and, optionally after further purification, can be forwarded for certain end-use applications, such as the production of polyesters, either alone or in combination with 4,4' DMBP-rich third stream or a product thereof Conversion of 2,X'-Dimethylbiphenyl Isomers In some embodiments, part or all of the 2,X'-dimethylbiphenyl (DMBP) isomers in the second stream described above, either alone or together with part or all 3,3' dimethylbiphenyl present in the second stream, can be processed to increase the concentration of 3,4' and 4,4' dimethylbiphenyl (DMBP) in the second stream. One suitable process comprises a combination of hydrogenation of the DMBP back to MCHT, followed by transalkylation of the MCHT with toluene and then dehydrogenation of the transalkylation product back to DMBP. Such a process is described in our co-pending U.S. Patent Application Ser. No. 62/012,024, both filed Jun. 13, 2014, the entire contents of which are incorporated by reference herein. In particular, it is found that steric issues favor the transalkylation of 1-methyl-2-(X-methylcyclohexyl)benzene (where X=2, 3 or 4) with toluene to produce 1-methyl-Y-(X-methylcyclohexyl)benzene (where Y=3 or 4 and X is the same position as the feed).

Particularly, where the DMBP is produced via hydroalkylation of toluene, this process of increasing 3,4' and 4,4' DMBP concentration can be achieved by recycling the second stream to the hydroalkylation/dehydrogenation sequence.

Oxidation of Dimethylbiphenyl Compounds to Carboxylic Acids

Any of the dimethylbiphenyl isomer-containing streams described above can be oxidized to produce the corresponding biphenyldicarboxylic acid or (methyl-phenyl)benzoic acid. The oxidation can be performed by any process known in the art, such as by reacting the methyl-substituted biphenyl compounds with an oxidant, such as oxygen, ozone or air, or any other oxygen source, such as hydrogen peroxide, in the presence of a catalyst and with or without a promoter such as Br at temperatures from 30° C. to 300° C., such as from 60° C. to 200° C. Suitable catalysts comprise Co or Mn or a combination of both metals.

Thus, oxidation of part or all of the 3,4'-DMBP and 4,4'-DMBP rich first stream can produce a mixture of biphenyldicarboxylic acid isomers comprising at least 50 wt %, preferably at least 80 wt %, preferably from 90 to 99 wt %, of a compound of the formula:

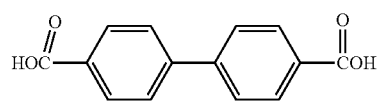

and and at least 1 wt %, such as up to 50 wt %, preferably from 1 to 10 wt %, of a compound of the formula:

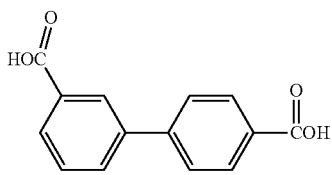

based on the total weight of biphenyldicarboxylic acids in the mixture.

Similarly, oxidation of part or all of the 4,4' DMBP-rich third stream can produce a mixture of biphenyldicarboxylic acid isomers comprising at least 70 wt %, preferably at least 80 wt %, preferably from 90 to 99 wt %, of a compound of the formula:

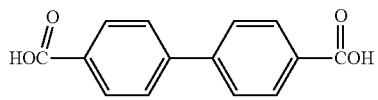

and and at least 1 wt %, preferably from 1 to 10 wt %, of a compound of the formula:

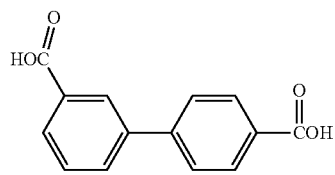

based on the total weight of biphenyldicarboxylic acids in the mixture.

In some cases, the oxidation can be conducted in the presence of p-xylene so that the oxidation product comprises terephthalic acid in addition to the mixtures of biphenyldicarboxylic acid isomers described above.

Hydrogenation of Carboxylic Acids

Any of the biphenyldicarboxylic acid and/or (methylphenyl)benzoic acid mixtures produced by the oxidation process described above, or their methyl esters, can be hydrogenated by methods known in the art to saturate one or both benzene rings and/or to convert one or both of the acid groups to an alcohol. Suitable hydrogenation conditions include, but are not limited to temperatures of 0-300° C., pressures of 1-500 atmospheres, and the presence of homogeneous or heterogeneous hydrogenation catalysts such as, but not limited to, platinum, palladium, ruthenium, nickel, zinc, tin, cobalt, copper, chromium, iron, or a combination of these metals, with palladium being particularly advantageous.

Thus, according to embodiments of the invention, such hydrogenation produces a mixture comprising at least 50 wt %, preferably from 90 to 99 wt %, of one or more compounds having the formulas:

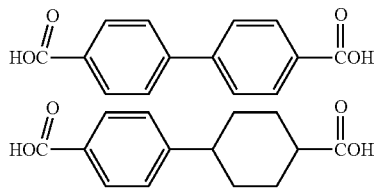

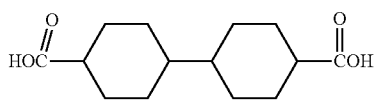

and at least 1 wt %, preferably from 1 to 10 wt %, of one or more compounds having the formulas:

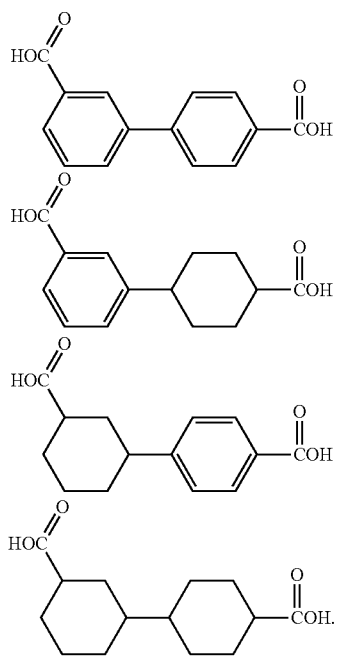

For example, such hydrogenation can produce a mixture of dicyclohexyldicarboxylic acids comprising at least 50 wt %, preferably from 90 to 99 wt %, of a compound having the formula:

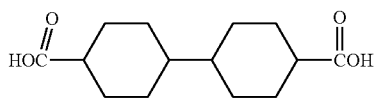

and at least 1 wt %, preferably from 1 to 10 wt %, of a compound having the formula:

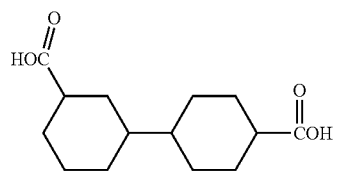

based on the total weight of dicyclohexyldicarboxylic acids in the mixture.

According to other embodiments of the invention, the hydrogenation produces a mixture comprising at least 50 wt %, preferably from 90 to 99 wt %, of one or more compounds having the formulas:

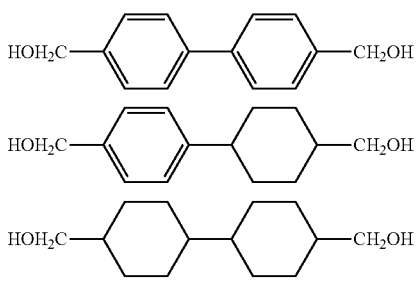

and at least 1 wt %, preferably from 1 to 10 wt %, of one or more compounds having the formulas:

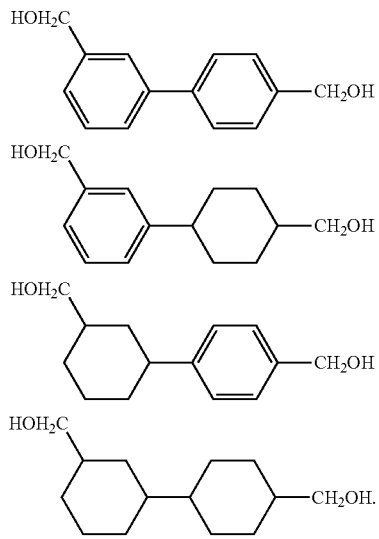

For example, such hydrogenation can produce a mixture of biphenyldialcohols comprising at least 50 wt %, preferably from 90 to 99 wt %, of a compound having the formula:

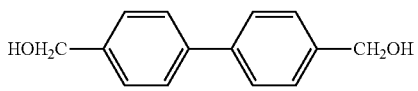 [SMILES: OCc1ccc(-c2ccc(CO)cc2)cc1]

and at least 1 wt %, preferably from 1 to 10 wt %, of a compound having the formula:

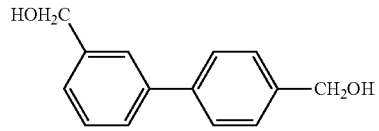

based on the total weight of biphenyldialcohols in the mixture.

In addition, the hydrogenation can produce a mixture dicyclohexyldialcohols comprising at least 50 wt %, preferably from 90 to 99 wt %, of compounds having the formula:

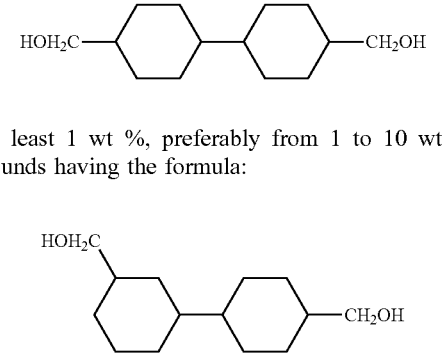

and at least 1 wt %, preferably from 1 to 10 wt %, of compounds having the formula:

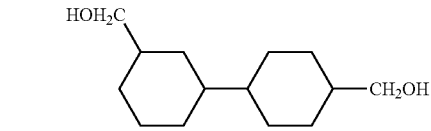

based on the total weight of dicyclohexyldialcohols in the mixture.

Production of Polyesters

Any of the biphenyldicarboxylic acid, phenylcyclohexyldicarboxylic acid and/or dicyclohexyldicarboxylic acid isomers and/or mixtures described above can be reacted with one or more diols and optionally with co-produced, or separately added, terephthalic acid to produce polyesters by any known method. For example, suitable biphenyldicarboxylic acid compositions include:

- 4,4' biphenyl dicarboxylic acid in a pure form or with less than 5% of 3,4' biphenyl dicarboxylic acid after separation;
- 3,4' biphenyl dicarboxylic acid in a pure form or with less than 5% of 4,4' biphenyl dicarboxylic acid after separation;
- a mixture of 3,4' and 4,4' biphenyl dicarboxylic acid where the molar ratio of 4,4' varies between 5% and 95%, and the molar ratio of 3,4' varies between 95% and 5%;
- a mixture of 4,4' biphenyl dicarboxylic acid and terephthalic acid wherein the molar ratio of 4,4' biphenyl dicarboxylic acid varies between 5% and 95%, and the molar ratio of terephthalic acid varies between 95% and 5%;
- a mixture of 3,4' biphenyl dicarboxylic acid and terephthalic acid wherein the molar ratio of 3,4' biphenyl dicarboxylic acid varies between 5% and 95%, and the molar ratio of terephthalic acid varies between 95% and 5%; and
- a mixture of 3,4' and 4,4' biphenyl dicarboxylic acids, preferably with more 4,4' than 3,4', for example, in 2:1 to 100:1 molar ratio, and terephthalic acid wherein the molar ratio of terephthalic acid varies between 95% and 5%.

Suitable diols for reaction with the above-mentioned diacid compositions include alkanediols having 2 to 12 carbon atoms, such as monoethylene glycol, diethylene glycol, 1,3-propanediol, or 1,4-butane diol, 1,6-hexanediol, and 1,4-cyclohexanedimethanol.

In addition, any of the biphenyldicarboxylic acid, phenylcyclohexyldicarboxylic acid and/or dicyclohexyldicarboxylic acid isomers and/or mixtures described above can be reacted with one or more of the mixtures of biphenyldialcohols, phenylcyclohexyldialcohols and/or dicyclohexyldialcohols described above to produce polyesters.

The polyesters may be prepared by conventional direct esterification or transesterification methods. Suitable catalysts include but not limited to titanium alkoxides such as titanium tetraisopropoxide, dialkyl tin oxides, antimony trioxide, manganese (II) acetate and Lewis acids. Suitable conditions include a temperature 170 to 350° C. for a time from 0.5 hours to 10 hours. Generally, the reaction is conducted in the molten state and so the temperature is selected to be above the melting point of the monomer mixture but below the decomposition temperature of the polymer. A higher reaction temperature is therefore needed for higher percentages of biphenyl dicarboxlic acid in the monomer mixture. The polyester may be first prepared in the molten state followed by a solid state polymerization to increase its molecular weight or intrinsic viscosity for applications like bottles.

In embodiments, the biphenyl dicarboxylic acids may be substituted by the corresponding biphenyl dicarboxylates (esters of corresponding biphenyl dicarboxylic acids), resulting in a transesterification reaction instead of direct esterification reaction.

Production of Monoesters and Diesters

Any of the biphenyldicarboxylic acid, phenylcyclohexyldicarboxylic acid and/or dicyclohexyldicarboxylic acid isomers and/or mixtures described above can also be reacted with one of more $C_1$ to $C_{16}$ alcohols to produce an esterification product. Suitable esterification conditions are well-known in the art and include, but are not limited to, temperatures of 0-300° C. and the presence or absence of homogeneous or heterogeneous esterification catalysts, such as Lewis or Bronsted acid catalysts. Suitable alcohols are "oxo-alcohols", by which is meant an organic alcohol, or mixture of organic alcohols, which is prepared by hydroformylating an olefin, followed by hydrogenation to form the alcohols. Typically, the olefin is formed by light olefin oligomerization over heterogeneous acid catalysts, which olefins are readily available from refinery processing operations. The reaction results in mixtures of longer-chain, branched olefins, which subsequently form longer chain, branched alcohols, as described in U.S. Pat. No. 6,274,756, incorporated herein by reference in its entirety. Another source of olefins used in the OXO process are through the oligomerization of ethylene, producing mixtures of predominately straight chain alcohols with lesser amounts of lightly branched alcohols.

One embodiment of a process of producing 4,4'-dimethylbiphenyl from a toluene-containing feed is illustrated in FIG. 1, in which toluene and hydrogen are fed by a single line 11 or, if preferred by separate lines (not shown), to a hydroalkylation unit 12. The hydroalkylation unit 12 contains a bed of a bifunctional catalyst which comprises a hydrogenation component and a solid acid alkylation component and which converts at least part of the toluene to (methylcyclohexyl)toluene (MCHT). The effluent from the hydroalkylation unit 12, comprising MCHT and unreacted toluene together with a small amount of di(methylcyclohexyl)toluene, is initially fed to a first distillation unit 13, where the di(methylcyclohexyl)toluene is removed as a heavy steam 14. The remainder of the hydroalkylation unit effluent is then fed to a dehydrogenation unit 15 where the MCHT is dehydrogenated to produce dimethylbiphenyl (DMBP) and hydrogen. The dehydrogenation effluent also contains unreacted toluene.

The effluent from the dehydrogenation unit 15 is then supplied to a rough-cut separation unit 16, such as a second distillation unit, where hydrogen is removed via line 17 and at least some of the toluene is removed via line 18. The hydrogen in line 17 is then recycled to the hydroalkylation unit 12 via line 19 and/or to the dehydrogenation unit 15 via line 21, while the toluene in line 18 is recycled to the hydroalkylation unit 12.

The raw DMBP-containing product leaving the separation unit 16 is then fed via line 23 to a third distillation unit 24 where further toluene impurity is removed via overhead line 25 to be merged with the impurity stream in line 18 and $C_{15}$+ heavies are removed as bottoms stream 26. In addition, the third distillation unit 24 separates the raw DMBP product into a first stream containing at least 50 wt % of 3,4' and 4,4' DMBP and at least one second stream comprising one or more 2,x' (where x' is 2', 3', or 4') and 3,3' DMBP isomers.

The 3,4' and 4,4' DMBP-containing first stream exits the third distillation unit 24 as a first side stream and is fed via line 27 to a 4,4'-DMBP separation unit 28, where a third stream rich in 4,4'-DMBP is crystallized out of the first stream and recovered in line 29. The remaining 4,4'-DMBP depleted fourth stream is collected by line 31 for recovery and/or further treatment.

The 2,x' and 3,3' DMBP-containing second stream exits the third distillation unit 24 as a second side stream and is recycled via line 34 to the hydroalkylation unit 12.

This invention further relates to:

1. A process for producing 3,4' and/or 4,4' dimethyl-substituted biphenyl compounds, the process comprising:
    (a1) contacting a feed comprising toluene with hydrogen in the presence of a hydroalkylation catalyst under conditions effective to produce a hydroalkylation reaction product comprising (methylcyclohexyl)toluenes;
    (b1) dehydrogenating at least part of the hydroalkylation reaction product in the presence of a dehydrogenation catalyst under conditions effective to produce a dehydrogenation reaction product comprising a mixture of dimethyl-substituted biphenyl isomers; and
    (c1) separating the dehydrogenation reaction product into at least a first stream containing at least 50% of 3,4' and 4,4' dimethylbiphenyl isomers by weight of the first stream and at least one second stream comprising one or more 2,X' (where X' is 2', 3', or 4') and 3,3' dimethylbiphenyl isomers.

2. A process for producing 3,4' and/or 4,4' dimethyl-substituted biphenyl compounds, the process comprising:
    (a2) contacting a feed comprising benzene with hydrogen in the presence of a hydroalkylation catalyst under conditions effective to produce a hydroalkylation reaction product comprising cyclohexylbenzenes;
    (b2) dehydrogenating at least part of the hydroalkylation reaction product in the presence of a dehydrogenation catalyst under conditions effective to produce a dehydrogenation reaction product comprising biphenyl;
    (c2) reacting at least part of the dehydrogenation reaction product with a methylating agent in the presence of an alkylation catalyst under conditions effective to produce a methylation reaction product comprising a mixture of dimethyl-substituted biphenyl isomers; and
    (d2) separating the methylation reaction product into at least a first stream containing at least 50% of 3,4' and 4,4' dimethylbiphenyl isomers by weight of the first stream and at least one second stream comprising one or more 2,X' (where X' is 2', 3', or 4') and 3,3' dimethylbiphenyl isomers.

3. The process of paragraph 1 or paragraph 2, wherein the hydroalkylation catalyst comprises an acidic component and a hydrogenation component.

4. The process of paragraph 3, wherein the acidic component of the hydroalkylation catalyst comprises a molecular sieve.

5. The process of paragraph 4, wherein the molecular sieve is selected from the group consisting of BEA, FAU and MTW structure type molecular sieves, molecular sieves of the MCM-22 family and mixtures thereof 6. The process of paragraph 4 or paragraph 5, wherein the molecular sieve comprises a molecular sieve of the MCM-22 family.
7. The process of any one of paragraphs 3 to 6, wherein the hydrogenation component of the hydroalkylation catalyst is selected from the group consisting of palladium, ruthenium, nickel, zinc, tin, cobalt and compounds and mixtures thereof
8. The process of any preceding paragraph, wherein the conditions of the contacting include a temperature from about 100° C. to about 400° C. and a pressure from about 100 to about 7,000 kPa.
9. The process of any preceding paragraph, wherein the molar ratio of hydrogen to toluene or benzene supplied to the contacting is from about 0.15:1 to about 15:1.
10. The process of any preceding paragraph, wherein the dehydrogenation catalyst comprises an element or compound thereof selected from Group 10 of the Periodic Table of Elements.
11. The process of paragraph 10, wherein the dehydrogenation catalyst further comprises tin or a compound thereof
12. The process of any preceding paragraph, wherein the dehydrogenation conditions include a temperature from about 200° C. to about 600° C. and a pressure from about 100 kPa to about 3550 kPa (atmospheric to about 500 psig).
13. A process for producing 3,4' and/or 4,4' dimethyl-substituted biphenyl compounds, the process comprising:
(a3) oxidizing a feed comprising benzene in the presence of a oxidative coupling catalyst under conditions effective to produce a oxidation reaction product comprising biphenyl;
(b3) reacting at least part of the oxidation reaction product with a methylating agent in the presence of an alkylation catalyst under conditions effective to produce a methylation reaction product comprising a mixture of dimethyl-substituted biphenyl isomers; and
(c3) separating the methylation reaction product into at least a first stream comprising at least 50% of 3,4' and 4,4' dimethylbiphenyl isomers by weight of the first stream and at least one second stream comprising one or more 2,X' (where X' is 2', 3', or 4') and 3,3' dimethylbiphenyl isomers.
14. The process of any preceding paragraph, wherein the separating comprises distillation and/or crystallization.
15. The process of any preceding paragraph and further comprising:
(e) converting at least part of the 2,X' dimethylbiphenyl isomers in the second stream to 3,4' and 4,4' dimethylbiphenyl isomers.
16. The process of any preceding paragraph and further comprising:
(f) separating the first stream into a third stream rich in 4,4' dimethylbiphenyl and a fourth stream comprising 3,4' dimethylbiphenyl.
17. The process of paragraph 16, wherein the separating (f) comprises crystallization.
18. The process of paragraph 16 or paragraph 17, wherein the separating (f) comprises adding a solvent, preferably a $C_3$ to $C_{12}$ aliphatic hydrocarbon, more preferably pentane and/or hexane, to the first stream.
19. The process of any one of paragraphs 16 to 18 and further comprising:
(g) separating the fourth stream into a fifth stream rich in 3,4 dimethylbiphenyl and a sixth stream containing 3,3' dimethylbiphenyl.
20. The process of paragraph 19, wherein the separating (g) comprises crystallization.
21. The process of paragraph 19 or paragraph 20, wherein the separating (g) comprises adding a solvent, preferably a $C_3$ to $C_{12}$ aliphatic hydrocarbon, more preferably pentane and/or hexane, to the fourth stream.
22. The process of any one of paragraphs 16 to 21 and further comprising:
(h) oxidizing at least part of the third stream to produce an oxidation product comprising biphenyl-4,4'-dicarboxylic acid.
23. The process of paragraph 22, wherein the oxidizing (h) is conducted in the presence of p-xylene such that the oxidation product also comprises terephthalic acid.
24. The process of paragraph 22 or paragraph 23 and further comprising:
(i) reacting at least part of the oxidation product with a diol to produce an polyester product.
25. The process of paragraph 22 or paragraph 23 and further comprising:
(j) reacting at least part of the oxidation product with a $C_1$ to $C_{16}$ alcohol to produce an esterification product.
26. The process of paragraph 22 or paragraph 23 and further comprising:
(k) hydrogenating at least part of the oxidation product.
27. A mixture comprising at least 50 wt %, preferably from 90 to 99 wt %, of a compound of the formula:

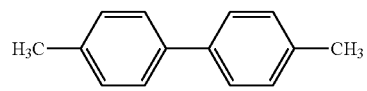

and at least 1 wt %, preferably from 1 to 10 wt %, of a compound of the formula:

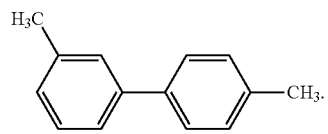

28. A mixture comprising at least 50 wt %, preferably from 90 to 99 wt %, of a compound of the formula:

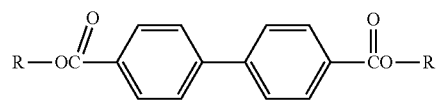

and at least 1 wt %, preferably from 1 to 10 wt %, of a compound of the formula:

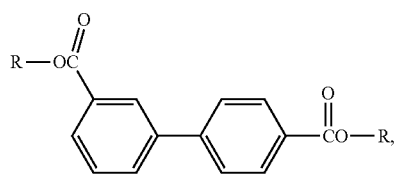

wherein each R is, independently, a $C_1$ to $C_6$ hydrocarbyl.
29. A mixture comprising at least 50 wt %, preferably from 90 to 99 wt %, of one or more compounds having the formulas:

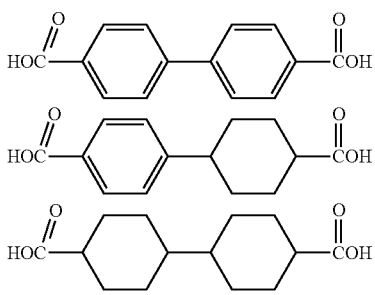

and at least 1 wt %, preferably from 1 to 10 wt %, of one or more compounds having the formulas:

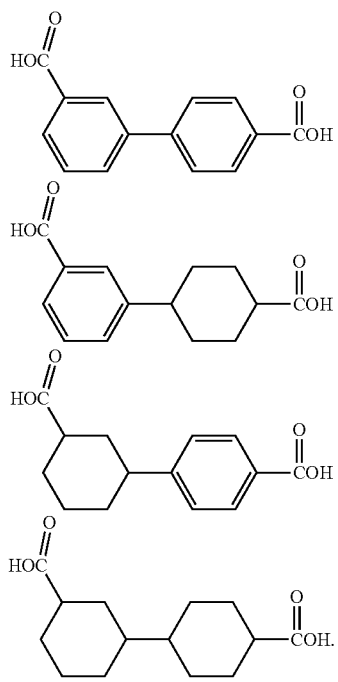

30. A polyester produced from the mixture of paragraph 29, a diol and optionally terephthalic acid.
31. A mixture comprising at least 50 wt %, preferably from 90 to 99 wt %, of a compound of the formula:

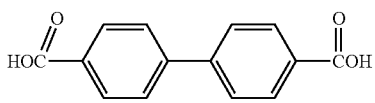

and at least 1 wt %, preferably from 1 to 10 wt %, of a compound of the formula:

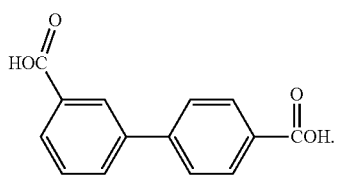

32. A polyester produced from the mixture of paragraph 31, a diol and optionally terephthalic acid.
33. A mixture comprising at least 50 wt %, preferably from 90 to 99 wt %, of a compound of the formula:

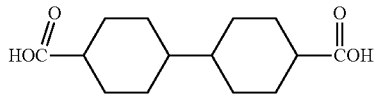

and at least 1 wt %, preferably from 1 to 10 wt %, of a compound of the formula:

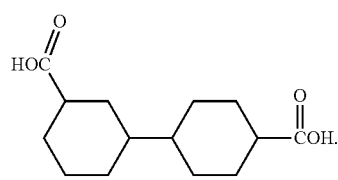

34. A polyester produced from the mixture of paragraph 33, a diol and optionally terephthalic acid.
35. A mixture comprising at least 50 wt %, preferably from 90 to 99 wt %, of one or more compounds having the formulas:

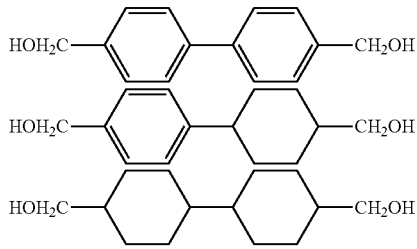

and at least 1 wt %, preferably from 1 to 10 wt %, of one or more compounds having the formulas:

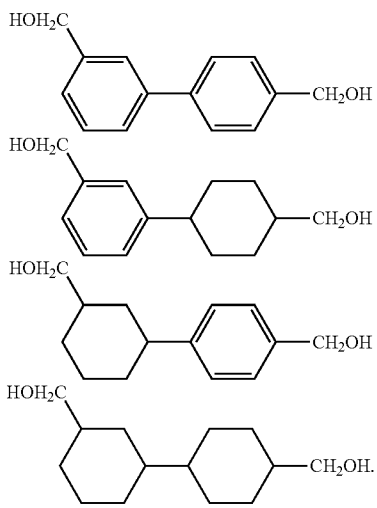

36. A polyester produced by reaction of at least one of the mixtures of paragraphs 29, 31 and 33 with the mixture of paragraph 35.

37. A mixture comprising at least 50 wt %, preferably from 90 to 99 wt %, of a compound of the formula:

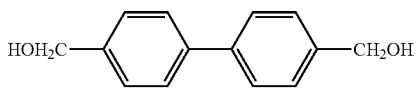

and at least 1 wt %, preferably from 1 to 10 wt %, of a compound of the formula:

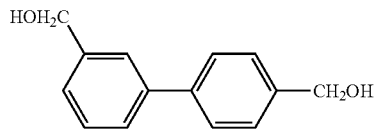 [SMILES: OCc1ccc(-c2cccc(CO)c2)cc1]

38. A polyester produced by reaction of at least one the mixtures of paragraphs 29, 31 and 33 with the mixture of paragraph 37.
39. A mixture comprising at least 50 wt %, preferably from 90 to 99 wt %, of a compound of the formula:

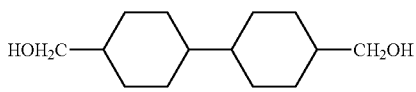

and at least 1 wt %, preferably from 1 to 10 wt %, of a compound of the formula:

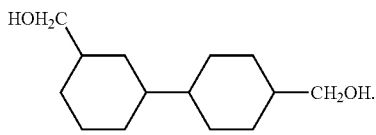 [SMILES: OCC1CCC(C2CCCC(CO)C2)CC1]

40. A polyester produced by reaction of at least one of the mixtures of paragraphs 29, 31 and 33 with the mixture of paragraph 39.

The invention will now be more particularly described with reference to the following non-limiting Examples.

EXAMPLE 1

Synthesis of 0.3% Pd/MCM-49 Hydroalkylation Catalyst 80 parts MCM-49 zeolite crystals are combined with 20 parts pseudoboehmite alumina, on a calcined dry weight basis. The MCM-49 and pseudoboehmite alumina dry powder are placed in a muller and mixed for about 10 to 30 minutes. Sufficient water and 0.05% polyvinyl alcohol is added to the MCM-49 and alumina during the mixing process to produce an extrudable paste. The extrudable paste is formed into a ¹⁄₂₀ inch (0.13 cm) quadrulobe extrudate using an extruder and the resulting extrudate is dried at a temperature ranging from 250° F. to 325° F. (120° C. to 163° C.). After drying, the dried extrudate is heated to 1000° F. (538° C.) under flowing nitrogen. The extrudate is then cooled to ambient temperature and humidified with saturated air or steam.

After the humidification, the extrudate is ion exchanged with 0.5 to 1 N ammonium nitrate solution. The ammonium nitrate solution ion exchange is repeated. The ammonium nitrate exchanged extrudate is then washed with deionized water to remove residual nitrate prior to calcination in air. After washing the wet extrudate, it is dried. The exchanged and dried extrudate is then calcined in a nitrogen/air mixture to a temperature 1000° F. (538° C.). Afterwards, the calcined extrudate is cooled to room temperature. The 80% MCM-49, 20% Al$_2$O$_3$ extrudate is incipient wetness impregnated with a palladium (II) chloride solution (target: 0.30% Pd) and then dried overnight at 121° C. The dried catalyst is calcined in air at the following conditions: 5 volumes air per volume catalyst per minute, ramp from ambient to 538° C. at 1° C./min and hold for 3 hours.

EXAMPLE 2

Synthesis of 0.3% Pd/Beta Hydroalkylation Catalyst 80 parts beta zeolite crystals are combined with 20 parts pseudoboehmite alumina, on a calcined dry weight basis. The beta and pseudoboehmite are mixed in a muller for about 15 to 60 minutes. Sufficient water and 1.0% nitric acid is added during the mixing process to produce an extrudable paste. The extrudable paste is formed into a ¹⁄₂₀ inch quadrulobe extrudate using an extruder. After extrusion, the ¹⁄₂₀th inch quadrulobe extrudate is dried at a temperature ranging from 250° F. to 325° F. (120° C. to 163° C.). After drying, the dried extrudate is heated to 1000° F. (538° C.) under flowing nitrogen and then calcined in air at a temperature of 1000° F. (538° C.). Afterwards, the calcined extrudate is cooled to room temperature. The 80% Beta, 20% Al$_2$O$_3$ extrudate is incipient wetness impregnated with a tetraammine palladium (II) nitrate solution (target: 0.30% Pd) and then dried overnight at 121° C. The dried catalyst is calcined in air at the following conditions: 5 volumes air per volume catalyst per minute, ramp from ambient to 538° C. at 1° C./min and hold for 3 hours

EXAMPLE 3

Synthesis of 0.3% Pd/USY Catalyst 80 parts Zeolyst CBV-720 ultrastable Y zeolite crystals are combined with 20 parts pseudoboehmite alumina on a calcined dry weight basis. The USY and pseudoboehmite are mixed for about 15 to 60 minutes. Sufficient water and 1.0% nitric acid is added during the mixing process to produce an extrudable paste. The extrudable paste is formed into a ¹⁄₂₀ inch quadrulobe extrudate using an extruder. After extrusion, the ¹⁄₂₀th inch quadrulobe extrudate is dried at a temperature ranging from 250° F. to 325° F. (120° C. to 163° C.). After drying, the dried extrudate is heated to 1000° F. (538° C.) under flowing nitrogen and then calcined in air at a temperature of 1000° F. (538° C.). The 80% CBV-720 USY, 20% Al$_2$O$_3$ extrudate is incipient wetness impregnated with a palladium (II) chloride solution (target: 0.30% Pd) and then dried overnight at 121° C. The dried catalyst is calcined in air at the following conditions: 5 volumes air per volume catalyst per minute, ramp from ambient to 538° C. at 1° C./min and hold for 3 hours.

EXAMPLE 4

Synthesis of 0.3% Pd/W—Zr Catalyst

A WO$_3$/ZrO$_2$ extrudate (11.5% W, balance Zr) ¹⁄₁₆" cylinder is obtained from Magnesium Elektron in the form of a 1/16 inch (0.16 cm) diameter extrudate. The $WO_3/ZrO_2$ extrudate is calcined in air for 3 hours at 538° C. On cooling, the calcined extrudate is incipient wetness impregnated with a palladium (II) chloride solution (target: 0.30% Pd) and then dried overnight at 121° C. The dried catalyst is calcined in air at the following conditions: 5 volumes air per volume catalyst per minute, ramp from ambient to 538° C. at 1° C./min and hold for 3 hours.

EXAMPLE 5

Hydroalkylation Catalyst Testing

Each of the catalysts of Examples 1 and 2 was tested in the hydroalkylation of a toluene or benzene feed using the reactor and process described below. The reactor comprised a stainless steel tube having an outside diameter of 3/8 inch (0.95 cm), a length of 20.5 inch (52 cm) and a wall thickness of 0.35 inch (0.9 cm). A piece of stainless steel tubing having a length of 8 3/4 inch (22 cm) and an outside diameter of 3/8 inch (0.95 cm) and a similar length of 1/4 inch (0.6 cm) were used in the bottom of the reactor (one inside of the other) as a spacer to position and support the catalyst in the isothermal zone of the furnace. A 1/4 inch (0.6 cm) plug of glass wool was placed on top of the spacer to keep the catalyst in place. A 1/8 inch (0.3 cm) stainless steel thermo-well was placed in the catalyst bed to monitor temperature throughout the catalyst bed using a movable thermocouple.

The catalyst was sized to 20/40 sieve mesh or cut to 1:1 length to diameter ratio, dispersed with quartz chips (20/40 mesh) then loaded into the reactor from the top to a volume of 5.5 cc. The catalyst bed typically was 15 cm. in length. The remaining void space at the top of the reactor was filled with quartz chips, with a 1/4 plug of glass wool placed on top of the catalyst bed being used to separate quartz chips from the catalyst. The reactor was installed in a furnace with the catalyst bed in the middle of the furnace at a pre-marked isothermal zone. The reactor was then pressure and leak tested typically at 300 psig (2170 kPa).

The catalyst was pre-conditioned in situ by heating to 25° C. to 240° C. with H2 flow at 100 cc/min and holding for 12 hours. A 500 cc ISCO syringe pump was used to introduce a chemical grade toluene feed to the reactor. The feed was pumped through a vaporizer before flowing through heated lines to the reactor. A Brooks mass flow controller was used to set the hydrogen flow rate. A Grove "Mity Mite" back pressure controller was used to control the reactor pressure typically at 150 psig (1135 kPa). GC analyses were taken to verify feed composition. The feed was then pumped through the catalyst bed held at the reaction temperature of 120° C. to 180° C. at a WHSV of 2 and a pressure of 15-200 psig (204-1480 kPa). The liquid products exiting the reactor flowed through heated lines routed to two collection pots in series, the first pot being heated to 60° C. and the second pot cooled with chilled coolant to about 10° C. Material balances were taken at 12 to 24 hrs intervals. Samples were taken and diluted with 50% ethanol for analysis. An Agilent 7890 gas chromatograph with FID detector was used for the analysis. The non-condensable gas products were routed to an on line HP 5890 GC.

The results of the hydroalkylation testing are summarized in FIGS. 2 to 6 and Table 2.

TABLE 2

| Example | Catalyst | Toluene conversion | Selectivity to methylcyclo- hexane | Selectivity to dimethylbi (cyclohexane) |
|---|---|---|---|---|
| 1 | 0.3% Pd/MCM49 | 37% | 23% | 1.40% |
| 2 | 0.3% Pd/Beta | 40% | 65% | 1.60% |
| 3 | 0.3% Pd/Y | 80% | 75% | 3.70% |
| 4 | 0.3% WO3/ZrO2 | 13% | 35% | 1.75% |

As can be seen from Table 2, although the Pd/MCM-49 catalyst is less active than the Pd/Y catalyst, it has much lower selectivity towards the production of the fully saturated by-products, methylcyclohexane and dimethylbi(cyclohexane) than either Pd/Y or Pd/beta. In addition, the data shown in FIG. 2 clearly demonstrate that Pd/MCM-49 provides the lowest yield loss, less than 1 wt % of total converted feed, to dialkylate products. The data shown in FIGS. 3 to 6 demonstrate that Pd/MCM-49 has improved stability and catalyst life as compared with the other catalysts tested. It is believed that the stability is related to the formation of heavies which remain on the surface of the catalyst and react further to create coke which prevents the access to the acid and hydrogenation sites.

Figure 7:
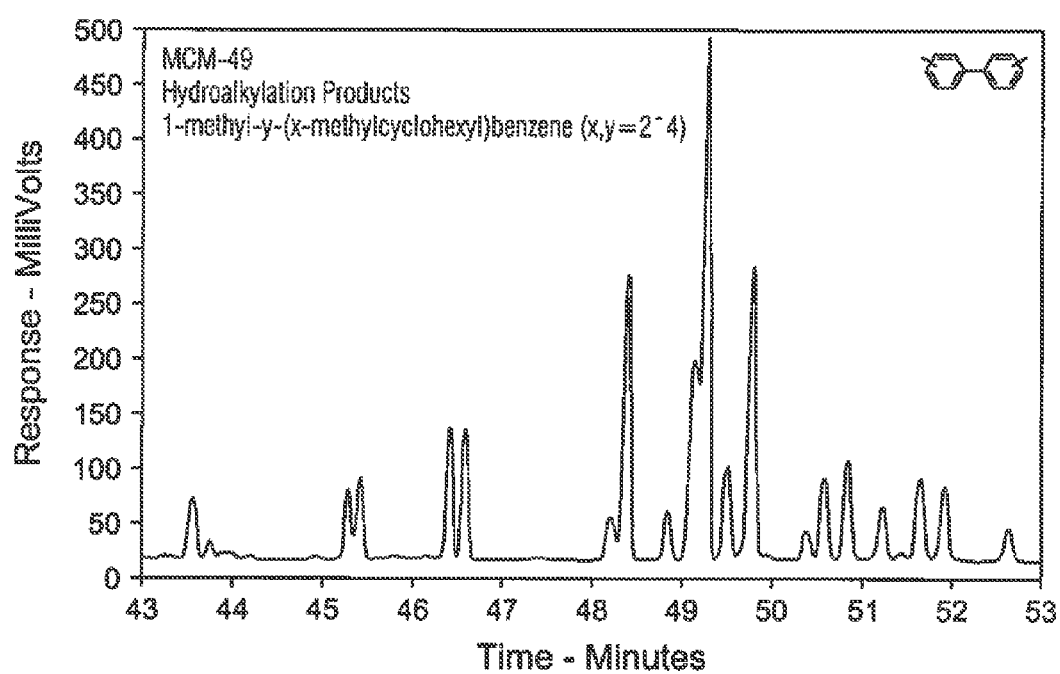
FIG. 7 is the GC spectrum of the product of hydroalkylation testing of the catalyst of Example 1 according to the process of Example 5.
Figure 8:
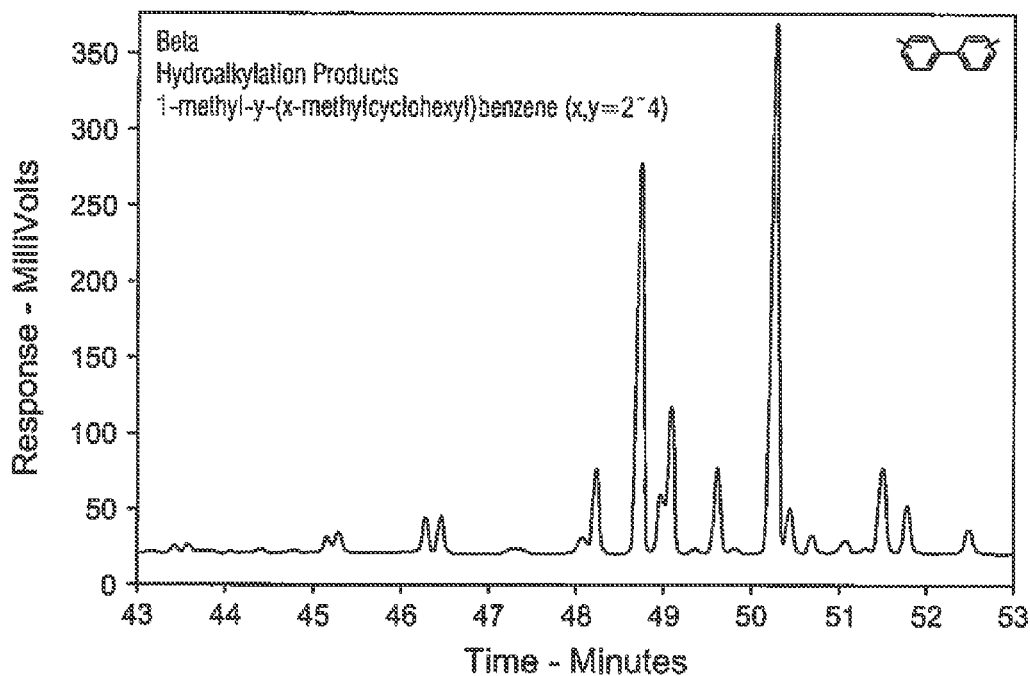
FIG. 8 is the GC spectrum of the product of hydroalkylation testing of the catalyst of Example 2 according to the process of Example 5.

The GC mass spectra in FIGS. 7 and 8, show that the hydroalkylated products obtained with the catalysts of Examples 1 and 2 contained the compounds listed in Table 3.

TABLE 3

|  | MCM-49 HA product | Beta HA product |
|---|---|---|
| y-(x-methylcyclohexyl)toluene (x, y = 2, 3, 4) | 89.29% | 39.82% |
| y-(1-methylcyclohexyl)toluene (y = 2, 4) | 3.03% | 53.26% |

Table 3 clearly shows that the MCM-49 catalyst can provide much higher amounts of the desired hydroalkylation products (y-(x-methylcyclohexyl)toluene (x,y=2, 3, 4)) than the zeolite beta catalyst, and much lower amounts of undesired y-(1-methylcyclohexyl)toluene (y=2, 4).

EXAMPLE 6

Production of 1% Pt/0.15% Sn/SiO2 Dehydrogenation Catalyst

A 1% Pt/0.15% Sn/SiO2 catalyst was prepared by incipient wetness impregnation, in which a 1/20" (1.2 mm) quadrulobe silica extrudate was initially impregnated with an aqueous solution of tin chloride and then dried in air at 121° C. The resultant tin-containing extrudates were then impregnated with an aqueous solution of tetraammine Pt nitrate and again dried in air at 121° C. The resultant product was calcined in air at 350° C. for 3 hours before being used in subsequent catalyst testing.

EXAMPLE 7

Preparation of 1% Pt/θ-Al$_2$O$_3$

θ-Al$_2$O$_3$ 2.5 mm trilobe extrudates were used as support for Pt deposition. The extrudates had a surface area of 126 m$^2$/g, pore volume of 0.58 cm$^3$/g, and pore size of 143 Å, as measured by BET N$_2$ adsorption. Pt was added to θ-Al$_2$O$_3$ support by impregnating with aqueous solution of $(NH_3)_4Pt(NO_3)_2$. The Pt metal loading on the supports is adjusted at 1 wt %. After impregnating, the sample was placed in the glass dish at room temperature for 60 minutes to reach equilibrium. Then it was dried in air at 250° F. (120° C.) for 4 hrs. The calcination was carried out in a box furnace at 680° F. (360° C.) in air for 3 hrs. The furnace was ramped at 3° F./minute. The air follow rate for the calcination was adjusted at 5 volume/volume catalyst/minute.

EXAMPLE 8

Preparation of 1% Pt+0.3% Sn/θ-$Al_2O_3$

The sample was prepared by sequential impregnations. $SnCl_2$ was added to θ-$Al_2O_3$ support by impregnation of aqueous solutions of tin chloride. The Sn metal oxide loading on the θ-$Al_2O_3$ support as Sn is 0.3 wt %. After impregnating, the sample was dried in air at 120° C. for 4 hrs. Pt was added to $Al_2O_3$ support containing Sn by impregnating with aqueous solutions of $(NH_3)_4Pt(NO_3)_2$. The Pt metal loading on the supports is 1 wt %. After impregnating, the sample was dried in air at 120° C. for 4 hrs, and then calcined at 360° C. in air for 3 hrs.

EXAMPLE 9

Preparation of 0.3% Pt+0.15% Sn/γ-$Al_2O_3$

γ-$Al_2O_3$ extrudates were also used to support Pt and Sn, which have surface area of 306 $m^2$/g, pore volume of 0.85 $cm^3$/g, and pore size of 73 Å. The Pt and Sn contents on γ-$Al_2O_3$ extrudates are 0.3% Pt/γ-$Al_2O_3$, and 0.3% Pt+0.15% Sn/γ-$Al_2O_3$.

EXAMPLE 10

Dehydrogenation Catalyst Testing without Feed Fractionation

The catalysts of Examples 6-8 were used to perform dehydrogenation testing on part of the effluent of the hydroalkylation reaction of Example 5. The same reactor and testing protocol as described in Example 5 were used to perform dehydrogenation tests, except the dehydrogenation catalyst was pre-conditioned in situ by heating to 375° C. to 460° C. with $H_2$ flow at 100 cc/min and holding for 2 hours. In addition, in the dehydrogenation tests, the catalyst bed was held at the reaction temperature of 375° C. to 460° C. at a WHSV of 2 and a pressure of 100 psig (790 kPa).

Figure 9:
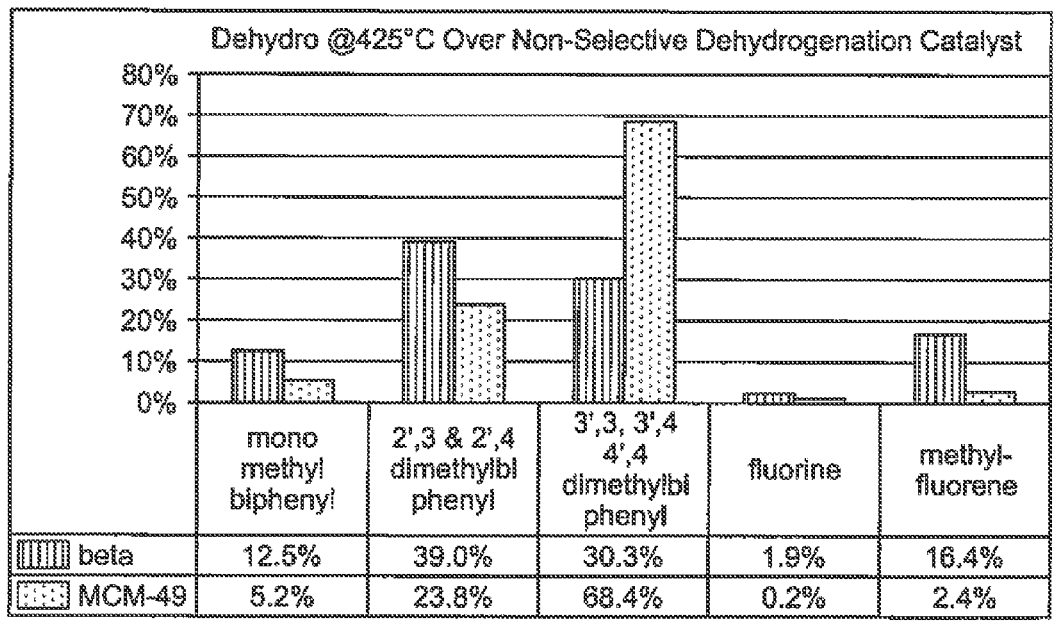
FIG. 9 is a bar graph comparing the reaction effluents produced by the non-selective dehydrogenation of the hydroalkylation products of Examples 1 and 2.
Figure 10:
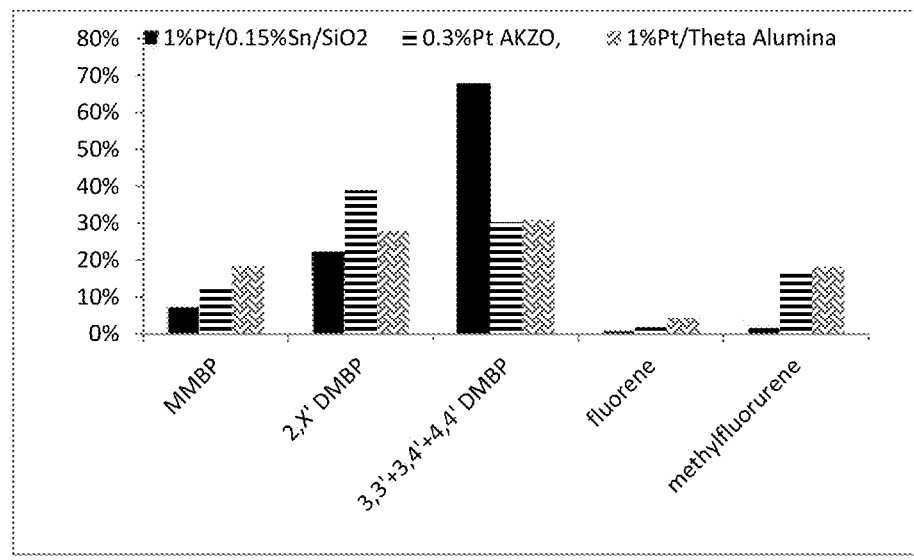
FIG. 10 is a bar graph comparing the product compositions obtained with the different dehydrogenation catalysts in the process of Example 10.

The analysis is done on an Agilent 7890 GC with 150 vial sample tray.
Inlet Temp: 220° C. Detector Temp: 240° C. (Col+make up=constant).
Temp Program: Initial temp 120° C. hold for 15 min., ramp at 2° C./min to 180° C., hold 15 min; ramp at 3° C./min. to 220° C. and hold till end. Column Flow: 2.25 ml/min. (27 cm/sec); Split mode, Split ratio 100:1.
Injector: Auto sampler (0.2 μl).
Column Parameters:
Two columns joined to make 120 Meters (coupled with Agilent ultimate union) deactivated.
Column # Front end: Supelco β-Dex 120; 60 m×0.25 mm×0.25 μm film joined to Column #2 back end: γ-Dex 325: 60 m×0.25 mm×0.25 μm film.
The results of the dehydrogenation testing are summarized in FIGS. 9 and 10. The data clearly shows that dehydrogenation of the MCM-49 hydroalkylation products provides less mono methyl biphenyl, less of the 2',3 and 2',4 isomers which are the precursors for the formation of fluorene and methyl fluorene and much less the fluorene and methyl fluorene as compared with dehydrogenation of the zeolite beta hydroalkylation products.

EXAMPLE 11

Oxidation of 4,4'DMBP Using 1000 ppm NaBr

Figure 11:
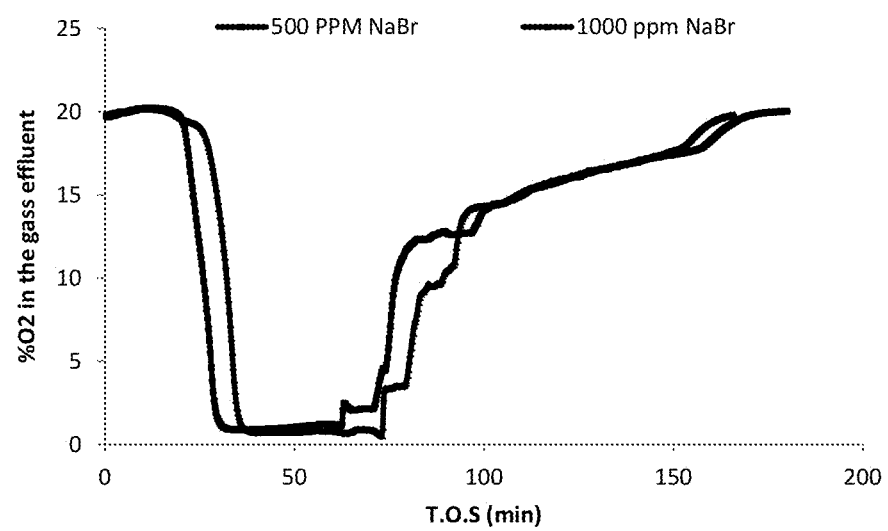
FIG. 11 is a graph plotting oxygen in the reaction effluent against time on stream for the oxidation reactions of Examples 11 and 12.

Oxidation was done batchwise. A 300 ml Parr reactor was charged with 50 grams of 4,4'dimethylbiphenyl, 150 gms acetic acid, 1500 ppm cobalt acetate, and 1000 ppm NaBr. The reactor was sealed and pressurized to 500 psig with nitrogen. The reactor was heated to 150° C. with a stir rate of 1200 rpm under 1500 cc/min $N_2$. When the temperature reached 150° C., $N_2$ was switched to air at the same flow rate. During the reaction oxygen concentration in the gas effluent was monitored and, as shown in FIG. 11, dropped to less than 2% after about 30 minutes on stream before returning to its initial value after about 250 minutes. After 3 hours reaction time the air flow was switched to $N_2$, and the reactor was cooled to room temperature then depressurized. The reactor was disassembled and the contents removed and analyzed by GC. The conversion is 100% and the selectivity to diacid >98%, less than 0.1% aldehyde acid and the rest is mono acid.

EXAMPLE 12

Oxidation of 4,4'DMBP Using 500 ppm NaBr

Oxidation was again done batchwise. A 300 ml Parr reactor was charged with 50 grams of 4,4'dimethylbiphenyl, 150 gms acetic acid, 1500 ppm Co acetate, and 500 ppm NaBr. The reactor was sealed and pressurized to 500 psig with nitrogen. The reactor was heated to 150° C. with a stir rate of 1200 rpm under 1500 cc/min $N_2$. When the temperature reached 150° C., $N_2$ was switched to air at the same flow rate. During the reaction, oxygen concentration dropped to less than 2% in the gas effluent (see FIG. 11). After 3 hours reaction time, the air flow was switched to $N_2$, and the reactor was cooled to room temperature; then depressurized. The reactor was disassembled and the contents removed and analyzed by GC. The conversion is 100% and the selectivity to diacid >95%, less than 0.5% aldehyde acid and the rest is mono acid.

EXAMPLE 13

Oxidation of Mixed 4,4'DMBP and P-Xylene in the Presence of NaBr

Oxidation was done batchwise. A 300 ml Parr reactor was charged with 15 grams of 4,4'dimethylbiphenyl, 15 grams p-xylene, 120 grams acetic acid, 1500 ppm Co acetate, and 500 ppm NaBr. The reactor was sealed and pressurized to 500 psig with nitrogen. The reactor was heated to 150° C. with a stir rate of 1200 rpm under 1500 cc/min $N_2$. When the temperature reached 150° C., $N_2$ was switched to air at the same flow rate. During the reaction, oxygen concentration dropped to less than 2% in the gas effluent. After 2 hours reaction time, the air flow was switched to $N_2$, reactor was cooled to room temperature, then depressurized. The reactor was disassembled and the contents removed and analyzed by GC. P-xylene and dimethylbiphenyl conversion is 100%.

The selectivity to terephthalic acid is 99%, less than 0.1% aldehyde acid and the rest is mono acid. The selectivity to biphenyl diacid is >98%, less than 0.2% aldehyde acid and the rest is mono acid.

EXAMPLE 14

Oxidation of 4,4'DMBP without Bromide

Figure 12:
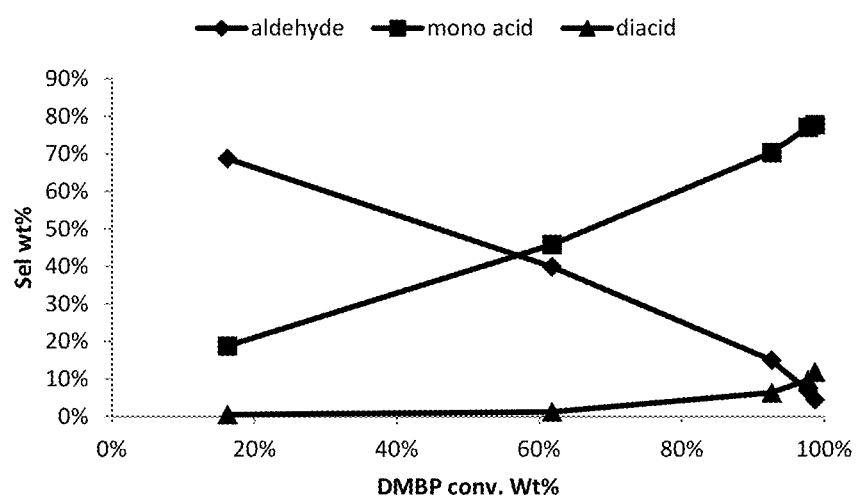
FIG. 12 is a graph plotting 4,4'-DMBP conversion against selectivity to the corresponding aldehyde, monoacid and diacid for the process of Example 14.

Oxidation was done batchwise. A 300 ml Parr reactor was charged with 30 grams of 4,4'dimethylbiphenyl, 120 grams acetic acid, 1500 ppm Co acetate. The reactor was sealed and pressurized to 500 psig with nitrogen. The reactor was heated to 150° C. with a stir rate of 1200 rpm under 1500 cc/min $N_2$. When the temperature reached 150° C., $N_2$ was switched to air at the same flow rate. During the reaction, oxygen concentration dropped to less than 8% in the gas effluent. After 2 hours reaction time, the air flow was switched to $N_2$, the reactor was cooled to room temperature, then depressurized. The reactor was disassembled and the contents removed and analyzed by GC. The conversion/selectivity profile is shown in FIG. 12.

EXAMPLE 15

Preparation of Polyester

This example illustrates the preparation of a melt polyester by reaction of mono ethylene glycol with a mixture of 20% 4,4' biphenyl dicarboxylate and 80% terephthalic acid. The reaction is conducted in a flask equipped with a metal stirrer and in an atmosphere of nitrogen at a reaction temperature between 200 and 350° C., for example 200° C., first for 10 minutes to 3 hours, for example 2 hours, and then heated to 220° C. for 10 minutes to 3 hours, for example 2 hours, and then heated to 275-300° C., for example, 280° C. for 10 to 30 minutes, for example, 15 minutes, in the presence of 0.01 weight % of titanium butoxide. A vacuum of 0.1-1 mm Hg, for example 0.1 mm Hg, is then introduced and maintained between 10 minutes and 1 hour, for example 1 hour, while continuously stirring polymer, in order to remove glycol vapor and drive polycondensation equilibrium.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing 3,4'- and/or 4,4'-dimethyl-substituted biphenyl compounds, the process comprising:
   (a1) contacting a feed comprising toluene with hydrogen in the presence of a hydroalkylation catalyst under conditions effective to produce a hydroalkylation reaction product comprising (methylcyclohexyl)toluenes;
   (b1) dehydrogenating at least part of the hydroalkylation reaction product in the presence of a dehydrogenation catalyst under conditions effective to produce a dehydrogenation reaction product comprising a mixture of dimethyl-substituted biphenyl isomers; and
   (c1) separating the dehydrogenation reaction product into at least a first stream containing at least 50% of 3,4'- and 4,4'-dimethylbiphenyl isomers by weight of the first stream and at least one second stream comprising one or more 2,X'- where X' is 2', 3', or 4' and 3,3' dimethylbiphenyl isomers, wherein the hydroalkylation catalyst comprises an acidic component and a hydrogenation component and the acidic component of the hydroalkylation catalyst is a molecular sieve of the MCM-22 family.

2. The process of claim 1, wherein the hydrogenation component of the hydroalkylation catalyst is selected from the group consisting of palladium, ruthenium, nickel, zinc, tin, cobalt and compounds and mixtures thereof.

3. The process of claim 1, wherein the conditions of the contacting include a temperature from about 100° C. to about 400° C. and a pressure from about 100 to about 7,000 kPa and a molar ratio of hydrogen to toluene supplied to the contacting is from about 0.15:1 to about 15:1.

4. The process of claim 1, wherein the dehydrogenation catalyst comprises an element or compound thereof selected from Group 10 of the Periodic Table of Elements.

5. The process of claim 4, wherein the dehydrogenation catalyst further comprises tin or a compound thereof.

6. The process of claim 1, wherein the dehydrogenation conditions include a temperature from about 200° C. to about 600° C. and a pressure from about 100 kPa to about 3550 kPa.

7. The process of claim 1, wherein the separating comprises distillation and/or crystallization.

8. The process of claim 1, further comprising:
   (e) converting at least part of the 2,X'-dimethylbiphenyl isomers in the second stream to 3,4'- and 4,4'-dimethylbiphenyl isomers.

9. The process of claim 1, further comprising:
   (f) separating the first stream into a third stream rich in 4,4'-dimethylbiphenyl and a fourth stream comprising 3,4'-dimethylbiphenyl.

10. The process of claim 9, wherein the separating (f) comprises crystallization and/or adding a solvent to the first stream.

11. The process of claim 9, further comprising:
    (g) separating the fourth stream into a fifth stream rich in 3,4-dimethylbiphenyl and a sixth stream containing 3,3'-dimethylbiphenyl.

12. The process of claim 11, wherein the separating (g) comprises crystallization and/or adding a solvent to the fourth stream.

13. The process of claim 9, further comprising:
    (h) oxidizing at least part of the third stream to produce an oxidation product comprising biphenyl-4,4'-dicarboxylic acid.

14. The process of claim 13, wherein the oxidizing (h) is conducted in the presence of p-xylene such that the oxidation product also comprises terephthalic acid.

15. The process of claim 13, further comprising:
    (i) reacting at least part of the oxidation product with a diol to produce a polyester product.

16. The process of claim 13, further comprising:
    (j) reacting at least part of the oxidation product with a $C_1$ to $C_{16}$ alcohol to produce an esterification product.

17. The process of claim 13, further comprising:
    (k) hydrogenating at least part of the oxidation product.

* * * * *